United States Patent [19]

Douglas et al.

[11] 4,443,456
[45] Apr. 17, 1984

[54] PYRIDYL ALKYLENE AMIDINOUREAS

[75] Inventors: George H. Douglas, Malvern; William L. Studt, Harleysville; Stuart A. Dodson, Lansdale; Harry K. Zimmerman, Quakertown, all of Pa.

[73] Assignee: William H. Rorer, Inc., Fort Washington, Pa.

[21] Appl. No.: 262,808

[22] Filed: May 12, 1981

[51] Int. Cl.³ .................. A61K 31/44; C07D 213/46
[52] U.S. Cl. ............................. 424/263; 546/331; 546/332; 546/288; 546/289; 546/286; 546/290; 546/294; 546/295; 546/296; 546/297; 546/298; 546/299; 546/304; 546/307; 546/308; 546/309; 546/310; 546/318; 546/314; 546/315; 546/321
[58] Field of Search ............. 546/331, 332, 288, 289, 546/286, 290, 294, 295, 296, 297, 298, 299, 304, 307, 309, 310, 318, 314, 315, 321; 424/263

[56] References Cited

U.S. PATENT DOCUMENTS

| | | | |
|---|---|---|---|
| 3,905,984 | 9/1975 | Durant et al. | 546/331 |
| 3,931,203 | 1/1976 | Kilbourn et al. | 546/331 |
| 4,098,898 | 7/1978 | Durant et al. | 546/331 |
| 4,225,315 | 9/1980 | Won et al. | 544/197 |
| 4,246,409 | 1/1981 | Douglas et al. | 544/211 |
| 4,358,447 | 11/1982 | Hannah | 424/246 |

FOREIGN PATENT DOCUMENTS

| | | | |
|---|---|---|---|
| 1461806 | 1/1977 | United Kingdom | 546/331 |
| 2039891 | 8/1980 | United Kingdom . | |

Primary Examiner—Jane T. Fan
Attorney, Agent, or Firm—James A. Nicholson; Alexis Barron; Martin F. Savitzky

[57] ABSTRACT

This invention relates to a novel class of amidinourea and amidinothiourea compounds wherein the urea nitrogen atom is substituted by a heterocyclic alkylene group, and their use in pharmaceutical preparations which are useful for producing anti-ulcerogenic, antisecretory, antispasmodic, antihypertensive, anesthetic, anti-arrhythmic, antidiarrheal and antiparasitic action.

14 Claims, No Drawings

PYRIDYL ALKYLENE AMIDINOUREAS

FIELD OF THE INVENTION

This invention relates to a novel class of heterocyclic alkylene substituted amidinoureas and amidinothioureas and their pharmaceutical use in methods for producing gastrointestinal, cardiovascular, and antiparasitic action, among others.

REPORTED DEVELOPMENTS

Phenylamidinoureas and their uses as antisecretory, antispasmodic, anti-ulcerogenic, anesthetic and antidiarrheal agents have been reported in *Arzneimittel Forschung* (Drug Research) 28 (II), 1433–1480 (1978), and U.S. Pat. Nos. 4,025,,652, 4,058,557, 4,060,635, 4,088,785, 4,115,564, 4,115,647, 4,117,165, 4,147,804, 4,150,154, 4,169,155, 4,178,387, 4,204,000 and 4,220,658.

This invention relates to a class of heterocyclic alkylene amidinourea and thiourea compounds which also possess valuable pharmaceutical properties.

SUMMARY OF THE INVENTION

This invention pertains to a novel class of heterocyclic alkylene substituted amidinourea and thiourea compounds, according to Formula I and processes for their synthesis. This invention also relates to the treatment of humans and animals afflicted with gastrointestinal disorders, spasmolytic disorders, ulcerogenic disorders, cardiovascular disorders, diarrheal disorders, and parasitic infestations of the blood and blood-forming organs with compositions containing an effective amount of heterocyclic alkylene substituted amidinourea or thiourea according to formula I.

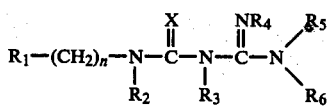

where:
X is O or S;
n is 1 to 3;
$R_1$ is a 5 to 7 atom ring or a 7 to 13 atom fused or bridged ring which may include 1 to 4 hetero atoms of N, O or S; and containing a total of about 3 to about 20 carbon atoms; and the N— or S— oxides thereof;
$R_2$, $R_3$ and $R_4$ are hydrogen or lower alkyl;
$R_5$ and $R_6$ are hydrogen, alkyl, cycloalkyl, aralkyl, aryl, alkenyl, alkoxy or a heterocyclic group, or $R_5$ and $R_6$ together with the nitrogen to which they are attached form a 3 to 7 atom ring which may include 0 to 2 additional hetero atoms of N, O or S; and the nontoxic acid addition salts thereof.

DETAILED DESCRIPTION OF THE INVENTION

Exemplary embodiments of this invention comprise compounds according to Formula I in which $R_1$ is one of the following heterocyclic groups: 1-pyrrole, 2-pyrrole, 3-pyrrole, 2-furan, 3-furan, 2-thiophene, 3-thiophene, 2-tetrahydrothiophene, 3-tetrahydrothiophene, 1-imidizole, 2-imidizole, 4-imidizole, 5-imidizole, 2-oxazole, 4-oxazole, 5-oxazole, 2-thiazole, 4-thiazole, 5-thiazole, 1-pyrazole, 3-pyrazole, 4-pyrazole, 5-pyrazole, 1-pyrrolidine, 2-pyrrolidine, 3-pyrrolidine, 1-(3-pyrroline), 2-(3-pyrroline), 3-(3-pyrroline), 2-pyridyl, 3-pyridyl, 4-pyridyl, 2-pyrimidine, 4-pyrimidine, 5-pyrimidine, 6-pyrimidine, 2-purine, 6-purine, 8-purine, 9-purine 2-quinoline, 3-quinoline, 4-quinoline, 5-quinoline, 6-quinoline, 7-quinoline, 8-quinoline, 1-isoquinoline, 3-isoquinoline, 4-isoquinoline, 5-isoquinoline, 6-isoquinoline, 7-isoquinoline, 8-isoquinoline, or carbazole.

The heterocyclic groups above may be mono-, di-, tri- or tetra-substituted by ring substituents, such as, halogen, lower alkyl, lower alkenyl, aryl, lower alkynyl, aralkyl, nitrol, cyano, sulfonyl, hydroxyl, carboxyl, lower alkanoyl, lower alkoxy, aryl lower alkoxy, halo lower alkoxy, amido, amino, lower alkyl acyloxy, alkylamino, lower alkoxyamino, and aralkoxyamino.

Compounds of this invention which are preferred include those according to Formula I where:
n is 1 or 2;
$R_1$ is a substituted or unsubstituted 5, 6 or 7 atom ring including 1 to 3 hetero atoms of N, O or S; and N— and S— oxides thereof;
$R_2$ is hydrogen or lower alkyl;
$R_3$ and $R_4$ are hydrogen;
$R_5$ and $R_6$ are hydrogen, lower alkyl, cycloalkyl, lower alkoxy, or aralkyl or $R_5$ and $R_6$ together with the nitrogen to which they are attached form a 3 to 7 atom heterocycle.

Another preferred embodiment of this invention according to formula I is wherein:
$R_1$ is one of the following heterocyclic groups

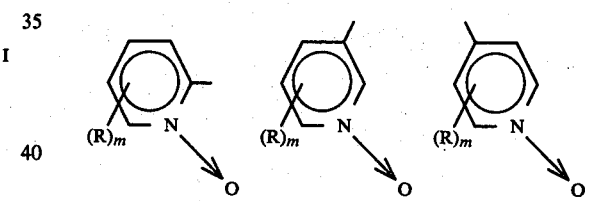

and,
m is zero to four;
R is a ring substituent selected from the group consisting of halogen, lower alkyl, lower alkenyl, aryl, lower alkynyl, aralkyl, nitro, cyano, sulfonyl, hydroxyl, carboxyl, lower alkanoyl, lower alkoxy, arly lower alkoxy, halo lower alkoxy, amido, amino, lower alkyl acyloxy, alkylamino, lower alkoxyamino, and aralkoxyamino or an acid addition salt thereof.

A most preferred embodiment of this invention is a compound according to Formulae II-IV

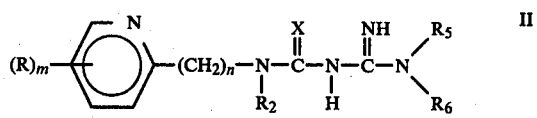

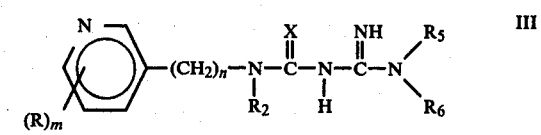

-continued

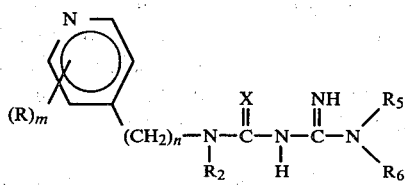

where:
X is O or S;
m is zero to four;
n is one or two;
R represents a ring substituent as described above, and the N-oxides of the pyridyl nitrogen atom; and
$R_2$, $R_5$ and $R_6$ are as described in Formula I above.
Preferred $R_5$ and $R_6$ groups are hydrogen, lower alkyl or lower alkoxy.

Another most preferred embodiment of this invention is a compound according to Formula V or VI

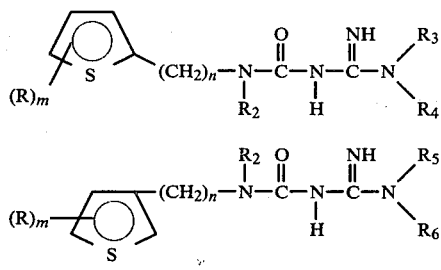

where:
m is zero to three
n is one or two;
R represents a ring substituent as described above; and the S-oxides of the thiophene sulfur atoms, such as, thiophenylsulfoxide and thiophenyl sulfone;
$R_2$, $R_5$ and $R_6$ are as defined above in Formula I;
and the nontoxic acid addition salts thereof.

In any discussion of the true structure of an amidinourea, tautomerism must be considered. It should be clear to anyone skilled in the art that the amidinourea chain can be legitimately represented in any one of several tautomeric forms. When the amidinourea is in solution, one form may predominate over another depending upon the degree and location of substitution and on the nature of the solvent. The rates of conversion of one tautomer to another will depend upon the nature of the solvent, the degree of hydrogen bonding permitted, the temperature, and possibly other factors (such as pH, trace impurities and the like).

To illustrate what is meant by this, a number of likely structures are here shown for just one of the compounds of this invention:

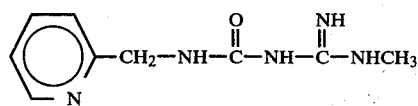

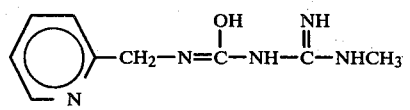

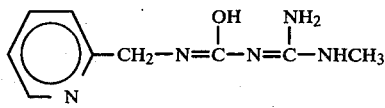

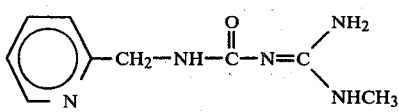

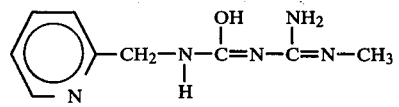

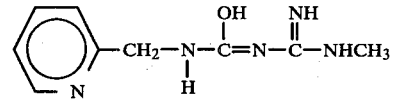

Of course, other structures are possible, such as those with hydrogen bonding.

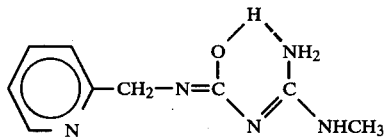

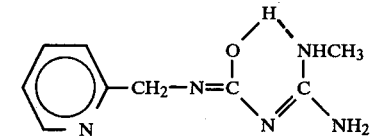

As employed above and throughout the disclosure, the following terms, unless otherwise indicated, shall be understood to have the following meanings:

"Alkyl" means a saturated aliphatic hydrocarbon which may be either straight- or branched-chain. Preferred groups have no more than about 12 carbon atoms and may be methyl, ethyl and structural isomers of propyl, butyl, phentyl, hexyl, heptyl, oxtyl, nonyl, decyl, undecyl and dodecyl. Also included are the cycloalkyl groups such as cyclopropyl, cyclopentyl, cyclohexyl, etc., and the cycloalkylalkyl groups such as cyclopropylmethyl and the like.

"Lower alkyl" means an alkyl group as above, having to 6 carbon atoms. Suitable lower alkyl groups are methyl, ethyl, n-propyl, isopropyl, butyl, sec-butyl, tert-butyl, n-pentyl, isopentyl and neopentyl.

"Cycloalkyl" means an aliphatic monocyclic saturated carbocyclic group having 3 to 6 carbon atoms. Preferred groups are cyclopropyl, cyclopentyl and cyclohexyl.

"Alkenyl" means an unsaturated aliphatic hydrocarbon. Preferred groups have no more than about 12 carbon atoms and 1 to 3 carbon-carbon double bonds and may include straight or branched chains, and may be any structural and geometric isomers of ethenyl, propylenyl, butenyl, pentenyl, hexenyl, heptenyl, octenyl, nonenyl, decenyl, undecenyl, and dodecenyl or butadienyl, pentadienyl etc. Also included are the cycloalkylene groups such as cyclopropenyl, cyclopentenyl, cyclohexenyl, etc. and the cycloalkylalkylene groups such as cyclopropylenylmethyl, cyclohexenylmethyl and the like.

"Lower alkenyl" means alkenyl or 2 to 6 carbon atoms such as ethylene, propylene, butylene, isobutylene, etc., including all structural and geometrical isomers thereof.

"Alkynyl" means an unsaturated aliphatic hydrocarbon. Preferred groups have no more than about 12 carbon atoms and contain one or more triple bonds, including any structural or geometric isomers of acetylenyl, propynyl, butynyl, pentynyl, hexynyl, heptynyl, octynyl, nonynyl, decynyl, undecynyl, dodecynyl, etc.

"Lower alkynyl" means alkynyl of 2 to 6 carbon atoms such as structural and geometric isomers of propargyl, butynyl, pentynyl, etc.

"Aryl" means phenyl and substituted phenyl.

"Substituted phenyl" means a phenyl group in which one or more of the hydrogens has been replaced by the same or different substituents including halo, lower alkyl, halo-lower alkyl, nitro, amino, acylamino, hydroxyl, lower alkoxy, aryl lower alkoxy, acyloxy, cyano, halo-lower alkoxy or lower alkyl sulfonyl. The preferred substituted phenyl group is phenyl in which the 2 and 6 positions are substituted.

"Aralkyl" means an alkyl (preferably a lower alkyl) in which one or more hydrogens is substituted by an aryl moiety (preferably phenyl or substituted phenyl), e.g., benzyl, phenethyl, etc.

"Heterocyclic group" or "heterocycle" means a 3, 5, 6 or 7 membered ring having 1 to 3 hetero atoms which may be nitrogen, oxygen or sulphur, including pyridyl, pyrimidyl, pyrazolyl, imidazolyl, furyl, thienyl, oxazoneyl, thiazolyl, piperidyl, morpholinyl, oxazolidinyl, thiazolidinyl, pyrazolidinyl, imidazolidinyl, piperazinyl, thiamorpholinyl, trimethylenetriaminyl and ethyleneiminyl; where the heterocycle may be mono-, di-, tri-or tetra-substituted by lower alkyl, lower alkenyl, lower alkynyl, aryl, aralkyl, halo, nitro, cyano, sulfonyl, hydroxyl, carboxyl, lower alkanoyl, lower carboalkoxy, lower alkoxy, aryl lower alkoxy, halo lower alkoxy, amido, amino, lower alkylamino, aralkylamino, lower alkoxyamino, and aralkylamino.

"Substituted heterocycle" means a heterocycle in which one or more of the hydrogens on the ring carbons have been replaced by substituents as given above with respect to substituted phenyl.

The terms "halo" and "halogen" include all four halogens; namely, fluorine, chlorine, bromine and iodine. The halo alkyls, halophenyl and halo-substituted pyridyl include groups having more than one halo substituent which may be the same or different such as trifluoromethyl, 1-chloro-2-bromo-ethyl, chlorophenyl, 4-chloropyridyl, etc.

"Acyloxy" means an organic acid radical of lower alkanoic acid such as acetoxy, propionoxy, and the like.

"Lower alkanoyl" means the acyl radical of a lower alkanoic acid such as acetyl, propionyl, butyryl, valeryl, stearoyl, and the like.

"Alkoxy" is intended to include hydroxy alkyl groups, preferably lower alkyl groups such as methoxy, ethoxy, n-propoxy, i-propoxy, and the like.

The preferred "aralkyl" groups are benzyl and phenethyl.

The preferred "halo lower alkyl" group is trifluoromethyl.

The preferred "halo lower alkoxy" group is trifluoromethoxy.

It is well known in the pharmacological arts that nontoxic acid addition salts of pharmacologically active amine compounds do not differ in activities from their free base. The salts merely provide a convenient solubility factor.

The amidinoureas of this invention may be readily converted to their nontoxic acid addition salts by customary methods in the art. The nontoxic salts of this invention are formed from the base amidinourea and an acid which is pharmacologically acceptable in the intended dosages. Such salts would include those prepared from inorganic acids, organic acids, higher fatty acids, high molecular weight acids, etc. Exemplary acids are hydrochloric acid, hydrobromic acid, sulfuric acid, nitric acid, phsophoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, etc.

Representative examples of the compounds of this invention are listed in Tables I and II.

TABLE I 1-(2'-pyridylmethyl)-3-methylamidinourea
1-(2'-pyridylmethyl)-3-ethylamidinourea
1-(2'-pryidylmethyl)-3-propylamidinourea
1-(2'-pyridylmethyl)-3-i-propylamidinourea
1-(2'-pyridylmethyl)-3-butylamidinourea
1-(2'-pyridylmethyl)-3-i-butylamidinourea
1-(2'-pyridylmethyl)-3-pentylamidinourea
1-(2'-pyridylmethyl)-3-propargylamidinourea
1-(2'-pyridylmethyl)-3-allylamidinourea
1-(2'-pyridylmethyl)-3-methoxyethylamidinourea
1-(2'-pyridylmethyl)-3-benzyloxyethylamidinourea
1-(2'-pyridylmethyl)-3-phenethoxyethylamidinourea
1-(2'-pyridylmethyl)-3-(N,N—dimethylamidino)urea
1-(2'-pyridylmethyl)-3-(N,N—diethylamidino)urea
1-(2'-pyridylmethyl)-3-(N,N—tetramethyleneamidino)urea
1-(2'-pyridylmethyl)-3-(N,N—pentamethyleneamidino)urea
1-(2'-pyridylmethyl)-3-(N,N—hexamethyleneamidino)urea
1-(3'-methyl-2'-pyridylmethyl)-3-methylamidinourea
1-(3'-methyl-2'-pyridylmethyl)-3-ethylamidinourea
1-(3'-methyl-2'-pyridylmethyl)-3-propylamidinourea
1-(3'-methyl-2'-pyridylmethyl)-3-i-propylamidinourea
1-(3'-methyl-2'-pyridylmethyl)-3-i-butylamidinourea
1-(3'-methyl-2'-pyridylmethyl)-3-pentylamidinourea
1-(3'-methyl-2'-pyridylmethyl)-3-allylamidinourea
1-(3'-methyl-2'-pyridylmethyl)-3-propargylamidinourea
1-(3'-methyl-2'-pyridylmethyl)-3-cyclopropylamidinourea
1-(3'-methyl-2'-pyridylmethyl)-3-methoxyethylamidinourea
1-(3'-methyl-2'-pyridylmethyl)-3-benzyloxyethylamidinourea
1-(3'-methyl-2'-pyridylmethyl)-3-phenethoxyethylamidinourea
1-(3'-methyl-2'-pyridylmethyl)-3-benzylamidinourea
1-(3'-methyl-2'-pyridylmethyl)-3-(N,N—dimethylamidino)urea
1-(3'-methyl-2'-pyridylmethyl)-3-(N,N—diethylamidino)urea
1-(3'-methyl-2'-pyridylmethyl)-3-(N,N—tetramethyleneamidino)urea
1-(3'-methyl-2'-pyridylmethyl)-3-(N,N—pentamethyleneamidino)urea
1-(3' -chloro-2'-pyridylmethyl)-3-methylamidinourea
1-(3'-chloro-2'-pyridylmethyl)-3-ethylamidinourea
1-(3'-chloro-2'-pyridylmethyl)-3-propylamidinourea
1-(3'-chloro-2'-pyridylmethyl)-3-i-propylamidinourea
1-(3'-chloro-2'-pyridylmethyl)-3-butylamidinourea
1-(3'-chloro-2'-pyridylmethyl)-3-i-butylamidinourea
1-(3'-chloro-2'-pyridylmethyl)-3-t-butylamidinourea
1-(3'-chloro-2'-pyridylmethyl)-3-pentylamidinourea
1-(3'-chloro-2'-pyridylmethyl)-3-allylamidinourea
1-(3'-chloro-2'-pyridylmethyl)-3-propargylamidinourea
1-(3'-chloro-2'-pyridylmethyl)-3-cyclopropylamidinourea
1-(3'-chloro-2'-pyridylmethyl)-3-cyclobutylamidinourea
1-(3'-chloro-2'-pyridylmethyl)-3-(N—[3'-cyclopentenyl]amidino)urea
1-(3'-chloro-2'-pyridylmethyl)-3-cyclopropylmethylamidinourea
1-(3'-chloro-2'-pyridylmethyl)-3-methoxyethylamidinourea
1-(3'-chloro-2'-pyridylmethyl)-3-benzyloxyethylamidinourea
1-(3'-chloro-2'-pyridylmethyl)-3-phenethoxyethylamidinourea
1-(3'-chloro-2'-pyridylmethyl)-3-benzylamidinourea
1-(3'-chloro-2'-pyridylmethyl)-3-(N,N—dimethylamidino)urea

TABLE I-continued 1-(3'-chloro-2'-pyridylmethyl)-3-(N,N—diethylamidino)urea
1-(3'-chloro-2'-pyridylmethyl)-3-(N,N—tetramethyleneamidino)urea
1-(2'-pyridylmethyl)-3-(N,N[3'-methyl-3'-azapentamethylene]amidino)urea
1-(2'-pyridylmethyl)-3-(N,N[3'-oxapentamethylene]amidino)urea
1-(3'-pyridylmethyl)-3-methylamidinourea
1-(3'-pyridylmethyl)-3-ethylamidinourea
1-(3'-pyridylmethyl)-3-propylamidinourea
1-(3'-pyridylmethyl)-3-i-propylamidinourea
1-(3'-pyridylmethyl)-3-butylamidinourea
1-(3'-pyridylmethyl)-3-i-butylamidinourea
1-(3'-pyridylmethyl)-3-t-butylamidinourea
1-(3'-pyridylmethyl)-3-pentylamidinourea
1-(3'-pyridylmethyl)-3-allylamidinourea
1-(3'-pyridylmethyl)-3-propargylamidinourea
1-(3'-pyridylmethyl)-3-cyclobutylamidinourea
1-(3'-pyridylmethyl)-3-cyclohexylamidinourea
1-(3'-pyridylmethyl)-3-benzylamidinourea
1-(3'-pyridylmethyl)-3-methoxyethylamidinourea
1-(3'-pyridylmethyl)-3-benzyloxyethylamidinourea
1-(3'-pyridylmethyl)-3-methoxyethylamidinourea
1-(3'-pyridylmethyl)-3-benzyloxyethylamidinourea
1-(3'-pyridylmethyl)-3-phenethoxyethylamidinourea
1-(3'-pyridylmethyl)-3-(N,N—dimethylamidino)urea
1-(3'-pyridylmethyl)-3-(N,N—diethylamidino)urea
1-(3'-pyridylmethyl)-3-(N,N—pentamethyleneamidino)urea
1-(4'-pyridylmethyl)-3-methylamidinourea
1-(4'-pyridylmethyl)-3-ethylamidinourea
1-(4'-pyridylmethyl)-3-propylamidinourea
1-(4'-pyridylmethyl)-3-i-propylamidinourea
1-(4'-pyridylmethyl)-3-butylamidinourea
1-(4'-pyridylmethyl)-3-t-butylamidinourea
1-(4'-pyridylmethyl)-3-pentylamidinourea
1-(4'-pyridylmethyl)-3-hexylamidinourea
1-(4'-pyridylmethyl)-3-propargylamidinourea
1-(4'-pyridylmethyl)-3-allylamidinourea
1-(4'-pyridylmethyl)-3-methoxyethylamidinourea
1-(4'-pyridylmethyl)-3-benzyloxyethylamidinourea
1-(4'-pyridylmethyl)-3-phenethoxyethylamidinourea
1-(4'-pyridylmethyl)-3-(N,N—dimethylamidino)urea
1-(4'-pyridylmethyl)-3-(N,N—diethylamidino)urea
1-(4'-pyridylmethyl)-3-(N—methyl-N—ethylamidino)urea
1-(4'-pyridylmethyl)-3-(N,N—tetramethyleneamidino)urea
1-(4'-pyridylmethyl)-3-(N,N—pentamethyleneamidino)urea
1-(4'-pyridylmethyl)-3-(N,N—hexamethyleneamidino)urea
1-(2'-ethyl-4'-pyridylmethyl)-3-methylamidinourea
1-(2'-ethyl-4'-pyridylmethyl)-3-ethylamidinourea
1-(2'-ethyl-4'-pyridylmethyl)-3-propylamidinourea
1-(2'-ethyl-4'-pyridylmethyl)-3-butylamidinourea
1-(2'-ethyl-4'-pyridylmethyl)-3-i-butylamidinourea
1-(2'-ethyl-4'-pyridylmethyl)-3-pentylamidinourea
1-(2'-ethyl-4'-pyridylmethyl)-3-allylamidinourea
1-(2'-ethyl-4'-pyridylmethyl)-3-propargylamidinourea
1-(2'-ethyl-4'-pyridylmethyl)-3-methoxyethylamidinourea
1-(2'-ethyl-4'-pyridylmethyl)-3-benzyloxyethylamidinourea
1-(2'-ethyl-4'-pyridylmethyl)-3-(N,N—dimethylamidino)urea
1-(2'-ethyl-4'-pyridylmethyl)-3-(N,N—diethylamidino)urea
1-(2'-ethyl-4'-pyridylmethyl)-3-(N,N—tetramethyleneamidino)urea
1-(2',6'-dichloro-4'-pyridylmethyl)-3-methylamidinourea
1-(2',6'-dimethyl-4'-pyridylmethyl)-3-methylamidinourea
1-(2'-methyl,6'-chloro-4'-pyridylmethyl)-3-methylamidinourea
1-(2'-thiophenylmethyl)-3-methylamidinourea
1-(3'-thiophenylmethyl)-3-methylamidinourea
1-(5'-methyl-2'-thiophenylmethyl)-3-methylamidinourea
1-(5'-chloro-2'-thiophenylmethyl)-3-methylamidinourea
1-(2'-pyridylmethyl-N—oxide)-3-(N,N—dimethylamidino)urea
1-(3'-cyano-2'-pyridylmethyl)-3-methylamidinourea
1-(3'-carbomethoxy-2'-pyridylmethyl-3-methylamidinourea
1-(3'-carboethoxy-2'-pyridylmethyl)-3-methylamidinourea
1-(6'-chloro-2'-pyridylmethyl)-3-methylamidinourea
1-(6'-methyl-2'-pyridylmethyl)-3-methylamidinourea
1-(3'-ethyl-2'-pyridylmethyl)-3-methylamidinourea
1-(2'-methyl-3'-pyridylmethyl)-3-(methylamidino)urea
1-(2'-ethyl-3'-pyridylmethyl)-3-(methylamidino)urea
1-(2',6'-dimethyl-3'-pyridylmethyl)-3-(methylamidino)urea
1-(3'-cyano-2'-thiophenylmethyl)-3-(methylamidino)urea
1-(3'-carbomethoxy-2'-thiophenylmethyl)-3-(methylamidino)urea
1-(3'-carboethoxy-2'-thiophenylmethyl)-3-(methylamidino)urea
1-(2'-methoxy-3'-pyridylmethyl)-3-(methylamidino)urea
1-(2'-ethoxy-3'-pyridylmethyl)-3-(methylamidino)urea
1-(2'-chloro-3'-pyridylmethyl)-3-(methylamidino)urea
1-furfuryl-3-amidinourea
1-(3'-methyl-furfuryl)-3-amidinourea
1-furfuryl-3-ethylamidinourea
1-furfuryl-3-propylamidinourea
1-furfuryl-3-i-propylamidinourea
1-furfuryl-3-butylamidinourea
1-furfuryl-3-i-butylamidinourea
1-furfuryl-3-sec-butylamidinourea
1-furfuryl-3-t-butylamidinourea
1-furfuryl-3-pentylamidinourea
1-furfuryl-3-hexylamidinourea
1-furfuryl-3-heptylamidinourea
1-furfuryl-3-cyclopropylamidinourea
1-furfuryl-3-cyclobutylamidinourea
1-(2'-pyridylmethyl-N—oxide)-3-methylamidinourea
1-(3'-pyridylmethyl-N—oxide)-3-methylamidinourea
1-(4'-pyridylmethyl-N—oxide)-3-methylamidinourea
1-furfuryl-3-methylamidinourea
1-tetrahydrofurfuryl-3-methylamidinourea
1-(1'-imidazolylmethyl)-3-methylamidinourea
1-(2'-imidazolylmethyl)-3-methylamidinourea
1-(4'-imidazolylmethyl)-3-methylamidinourea
1-(2'-oxazolylmethyl)-3-methylamidinourea
1-(4'-oxazolylmethyl)-3-methylamidinourea
1-(5'-oxazolylmethyl)-3-methylamidinourea
1-(2'-thiazolylmethyl)-3-methylamidinourea
1-(4'-thiazolylmethyl)-3-methylamidinourea
1-(5'-thiazolylmethyl)-3-methylamidinourea
1-(1'-pyrazolylmethyl)-3-methylamidinourea
1-(3'-pyrrolidinylmethyl)-3-methylamidinourea
1-(2'-pyrrolidinylmethyl)-3-methylamidinourea
1-(4'-morpholinylmethyl)-3-methylamidinourea
1-(2'-morpholinylmethyl)-3-methylamidinourea
1-(2'-pyrimidinylmethyl)-3-methylamidinourea
1-(4'-pyrimidinylmethyl)-3-methylamidinourea
1-(2'-quinolylmethyl)-3-methylamidinourea
1-(4'-quinolylmethyl)-3-methylamidinourea
1-(1'-isoquinolylmethyl)-3-methylamidinourea
1-(furfuryl-3-cyclopenylamidinourea
1-(furfuryl-3-cyclohexylamidinourea
1-(furfuryl-3-phenylamidinourea
1-(furfuryl-3-benzylamidinourea
1-(furfuryl-3-phenethylamidinourea
1-furfuryl-3-(N—methyl-N—benzylamidino)urea
1-furfuryl-3-(N,N—dibenzylamidino)urea
1-tetrahydrofurfuryl-3-amidinourea
1-(3'-methyl tetrahydrofurfuryl)-3-amidinourea
1-(1'-imidazolylmethyl)-3-amidinourea
1-(2'-methyl-1'-imidazolylmethyl)-3-amidinourea
1-(4'-imidazolylmethyl)-3-amidinourea
1-(1'-methyl-4'-imidazolylmethyl)-3-amidinourea
1-(2'-methyl-4'-imidazolylmethyl)-3-amidinourea
1-(2'-imidazolylmethyl)-3-amidinourea
1-(2'-oxazolylmethyl)-3-amidinourea
1-(4'-methyl-2'-oxazolylmethyl)-3-amidinourea
1-(4'-oxazolylmethyl)-3-amidinourea
1-(4'-methyl-2'-oxazolylmethyl)-3-amidinourea
1-(4'-oxazolylmethyl)-3-amidinourea
1-(2'-methyl-4'-oxazolylmethyl)-3-amidinourea
1-(5'-oxazolylmethyl)-3-amidinourea
1-(2'-methyl-5'-oxazolylmethyl)-3-amidinourea
1-(4'-thiazolylmethyl)-3-amidinourea
1-(5'-methyl-4'-thiazolylmethyl)-3-amidinourea
1-(5'-thiazolylmethyl)-3-amidinourea
1-(4'-methyl-5'-thiazolylmethyl)-3-amidinourea
1-(1'-pyrazolylmethyl)-3-amidinourea
1-(3'-pyrrolylmethyl)-3-amidinourea
1-(2'-methyl-3'-pyrrolylmethyl)-3-amidinourea
1-(3'-methyl-2'-pyrrolylmethyl)-3-amidinourea
1-(1'-pyrrolidinylmethyl)-3-amidinourea
1-(2'-methyl-1'-pyrrolidinylmethyl)-3-amidinourea
1-(1'-methyl-2'-pyrrolidinylmethyl)-3-amidinourea
1-(4'-morpholinylmethyl)-3-amidinourea
1-(2'-methyl-4'-morpholinylmethyl)-3-amidinourea
1-(2'-morpholinylmethyl)-3-amidinourea
1-(4'-methyl-2'-morpholinylmethyl)-3-amidinourea
1-(3'-methyl-2'-morpholinylmethyl)-3-amidinourea
1-(3'-morpholinylmethyl)-3-amidinourea
1-(4'-methyl-3'-morpholinylmethyl)-3-amidinourea
1-(2'-methyl-3'-mopholinylmethyl)-3-amidinourea
1-(2'-pyrimidinylmethyl)-3-amidinourea
1-(4'-methyl-2'-pyrimidinylmethyl)-3-amidinourea
1-(4'-pyrimidinylmethyl)-3-amidinourea

TABLE I-continued 1-(2'-methyl-4'-pyrimidinylmethyl)-3-amidinourea
1-(2'-quinolylmethyl)-3-amidinourea
1-(3'-methyl-2'-quinolylmethyl)-3-amidinourea
1-(4'-quinolylmethyl)-3-amidinourea
1-(3'-methyl-4'-quinolylmethyl)-3-amidinourea
1-(1'-isoquinolylmethyl)-3-amidinourea
1-[2-(2'-pyridyl)ethyl]-3-methylamidinourea
1-[2-(2'-pyridyl)ethyl]-3-ethylamidinourea
1-[2-(2'-pryidyl)ethyl]-3-propylamidinourea
1-[2-(2'-pyridyl)ethyl]-3-i-propylamidinourea
1-[2-(2'-pyridyl)ethyl]-3-butylamidinourea
1-[2-(2'-pyridyl)ethyl]-3-i-butylamidinourea
1-[2-(2'-pyridyl)ethyl]-3-pentylamidinourea
1-[2-(2'-pyridyl)ethyl]-3-propargylamidinourea
1-[2-(2'-pyridyl)ethyl]-3-allylamidinourea
1-[2-(2'-pyridyl)ethyl]-3-methoxyethylamidinourea
1-[2-(2'-pyridyl)ethyl]-3-benzyloxyethylamidinourea
1-[2-(2'-pyridyl)ethyl]-3-phenethoxyethylamidinourea
1-[2-(2'-pyridyl)ethyl]-3-(N,N—dimethylamidino)urea
1-[2-(2'-pyridyl)ethyl]-3-(N,N—diethylamidino)urea
1-[2-(2'-pyridyl)ethyl]-3-(N,N—tetramethyleneamidino)urea
1-[2-(2'-pyridyl)ethyl]-3-(N,N—pentamethyleneamidino)urea
1-[2-(2'-pyridyl)ethyl]-3-(N,N—hexamethyleneamidino)urea
1-[2-(3'-methyl-2'-pyridyl)ethyl]-3-methylamidinourea
1-[2-(3'-methyl-2'-pyridyl)ethyl]-3-ethylamidinourea
1-[2-(3'-methyl-2'-pyridyl)ethyl]-3-propylamidinourea
1-[2-(3'-methyl-2'-pyridyl)ethyl]-3-i-propylamidinourea
1-[2-(3'-methyl-2'-pyridyl)ethyl]-3-i-butylamidinourea
1-[2-(3'-methyl-2'-pyridyl)ethyl]-3-pentylamidinourea
1-[2-(3'-methyl-2'-pyridyl)ethyl]-3-allylamidinourea
1-[2-(3'-methyl-2'-pyridyl)ethyl]-3-propargylamidinourea
1-[2-(3'-methyl 2'-pyridyl)ethyl]-3-cyclopropylamidinourea
1-[2-(3'-methyl-2'-pyridyl)ethyl]-3-methoxyethylamidinourea
1-[2-(3'-methyl-2'-pyridyl)ethyl]-3-benzyloxyethylamidinourea
1-[2-(3'-methyl-2'-pyridyl)ethyl]-3-phenethoxyethylamidinourea
1-[2-(3'-methyl-2'-pyridyl)ethyl]-3-benzylamidinourea
1-[2-(3'-methyl-2'-pyridyl)ethyl]-3-(N,N—dimethylamidino)urea
1-[2-(3'-methyl-2'-pyridyl)ethyl]-3-(N,N—diethylamidino)urea
1-[2-(3'-methyl-2'-pyridyl)ethyl]-3-(N,N—tetramethyleneamidino)urea
1-[2-(3'-methyl-2'-pyridyl)ethyl] -3-(N,N—pentamethyleneamidino)urea
1-[2-(3'-chloro-2'-pyridyl)ethyl]-3-methylamidinourea
1-[2-(3'-chloro-2'-pyridyl)ethyl]-3-ethylamidinourea
1-[2-(3'-chloro-2'-pyridyl)ethyl]-3-propylamidinourea
1-[2-(3'-chloro-2'-pyridyl)ethyl]-3-i-propylamidinourea
1-[2-(3'-chloro-2'-pyridyl)ethyl]-3-butylamidinourea
1-[2-(3'-chloro-2'-pyridyl)ethyl]-3-i-butylamidinourea
1-[2-(3'-chloro-2'-pyridyl)ethyl]-3-t-butylamidinourea
1-[2-(3'-chloro-2'-pyridyl)ethyl]-3-pentylamidinourea
1-[2-(3'-chloro-2'-pyridyl)ethyl]-3-allylamidinourea
1-[2-(3'-chloro-2'-pyridyl)ethyl]-3-propargylamidinourea
1-[2-(3'-chloro-2'-pyridyl)ethyl]-3-cyclopropylamidinourea
1-[2-(3'-chloro-2'-pyridyl)ethyl]-3-cyclobutylamidinourea
1-[2-(3'-chloro-2'-pyridyl)ethyl]-3-(N—[3'-cyclopentenyl]amidino)urea
1-[2-(3'-chloro-2'-pyridyl)ethyl]-3-cyclopropylmethylamidinourea
1-[2-(3'-chloro-2'-pyridyl)ethyl]-3-methoxyethylamidinourea
1-[2-(3'-chloro-2'-pyridyl)ethyl]-3-benzyloxyethylamidinourea
1-[2-(3'-chloro-2'-pyridyl)ethyl]-3-phenethoxyethylamidinourea
1-[2-(3'-chloro-2'-pyridyl)ethyl]-3-benzylamidinourea
1-[2-(3'-chloro-2'-pyridyl)ethyl]-3-(N,N—dimethylamidino)urea
1-[2-(3'-chloro-2'-pyridyl)ethyl]-3-(N,N—diethylamidino)urea
1-[2-(3'-chloro-2'-pyridyl)ethyl]-3-(N,N—tetramethyleneamidino)urea
1-[2-(2'-pyridyl)ethyl]-3-(N,N[3'-methy-3'-azapentamethylene]amidino)urea
1-[2-(2'-pyridyl)ethyl]-3-(N,N[3'-oxapentamethylene]amidino)urea
1-[2-(2'-pyridyl)ethyl]-3-methylamidinourea
1-[2-(2'-pyridyl)ethyl]-3-ethylamidinourea
1-[2-(2'-pyridyl)ethyl]-3-propylamidinourea
1-[2-(2'-pyridyl)ethyl]-3-i-propylamidinourea
1-[2-(2'-pyridyl)ethyl]-3-butylamidinourea
1-[2-(2'-pyridyl)ethyl] -3-i-butylamidinourea
1-[2-(2'-pyridyl)ethyl]-3-t-butylamidinourea
1-[2-(2'-pyridyl)ethyl]-3-pentylamidinourea
1-[2-(2'-pyridyl)ethyl]-3-allylamidinourea
1-[2-(2'-pyridyl)ethyl]-3-propargylamidinourea
1-[2-(2'-pyridyl)ethyl]-3-cyclobutylamidinourea
1-[2-(2'-pyridyl)ethyl]-3-cyclohexylamidinourea
1-[2-(2'-pyridyl)ethyl]-3-benzylamidinourea
1-[2-(2'-pyridyl)ethyl]-3-methoxyethylamidinourea
1-[2-(2'-pyridyl)ethyl]-3-benzyloxyethylamidinourea
1-[2-(3'-pyridyl)ethyl]-3-methoxyethylamidinourea
1-[2-(3'-pyridyl)ethyl]-3-benzyloxyethylamidinourea
1-[2-(3'-pyridyl)ethyl]-3-phenethoxyethylamidinourea
1-[2-(3'-pyridyl)ethyl]-3-(N,N—dimethylamidino)urea
1-[2-(3'-pyridyl)ethyl]-3-(N,N—diethylamidino)urea
1-[2-(3'-pyridyl)ethyl]-3-(N,N—pentamethyleneamidino)urea
1-[2-(4'-pyridyl)ethyl]-3-methylamidinourea
1-[2-(4'-pyridyl)ethyl]-3-ethylamidinourea
1-[2-(4'-pyridyl)ethyl]-3-propylamidinourea
1-[2-(4'-pyridyl)ethyl]-3-i-propylamidinourea
1-[2-(4'-pyridyl)ethyl]-3-butylamidinourea
1-[2-(4'-pyridyl)ethyl]-3-t-butylamidinourea
1-[2-(4'-pyridyl)ethyl]-3-pentylamidinourea
1-[2-(4'-pyridyl)ethyl]-3-hexylamidinourea
1-[2-(4'-pyridyl)ethyl]-3-propargylamidinourea
1-[2-(4'-pyridyl)ethyl]-3-allylamidinourea
1-[2-(4'-pyridyl)ethyl]-3-methoxyethylamidinourea
1-[2-(4'-pyridyl)ethyl]-3-benzyloxyethylamidinourea
1-[2-(4'-pyridyl)ethyl]-3-phenethoxyethylamidinourea
1-[2-(4'-pyridyl)ethyl]-3-(N,N—dimethylamidino)urea
1-[2-(4'-pyridyl)ethyl]-3-(N,N—diethylamidino)urea
1-[2-(4'-pyridyl)ethyl]-3-(N—methyl-N—ethylamidino)urea
1-[3-(2'-pyridyl)propyl]-3-methylamidinourea
1-[3-(2'-pyridyl)propyl]-3-ethylamidinourea
1-[3-(2'-pyridyl)propyl]-3-propylamidinourea
1-[3-(2'-pyridyl)propyl] -3-i-propylamidinourea
1-[3-(2'-pyridyl)propyl]-3-butylamidinourea
1-[3-(2'-pyridyl)propyl]-3-i-butylamidinourea
1-[3-(2'-pyridyl)propyl]-3-pentylamidinourea
1-[3-(2'-pyridyl)propyl]-3-propargylamidinourea
1-[3-(2'-pyridyl)propyl]-3-allylamidinourea
1-[3-(2'-pyridyl)propyl]-3-methoxyethylamidinourea
1-[3-(2'-pyridyl)propyl]-3-benzyloxyethylamidinourea
1-[3-(2'-pyridyl)propyl]-3-phenethoxyethylamidinourea
1-[3-(2'-pyridyl)propyl]-3-(N,N—dimethylamidino)urea
1-[3-(2'-pyridyl)propyl]-3-(N,N—diethylamidino)urea
1-[3-(2'-pyridyl)propyl]-3-(N,N—tetramethyleneamidino)urea
1-[3-(2'-pyridyl)propyl]-3-(N,N—pentamethyleneamidino)urea
1-[3-(2'-pyridyl)propyl]-3-(N,N—hexamethyleneamidino)urea
1-[3-(3'-methyl-2'-pyridyl)propyl]-3-methylamidinourea
1-[3-(3'methyl-2'-pyridyl)propyl]-3-ethylamidinourea
1-[3-(3'-methyl-2'-pyridyl)propyl]-3-propylamidinourea
1-[3-(3'-methyl-2'-pyridyl)propyl]-3-i-propylamidinourea
1-[3-(3'-methyl-2'-pyridyl)propyl]-3-i-butylamidinourea
1-[3-(3'-methyl-2'-pyridyl)propyl]-3-pentylamidinourea
1-[3-(3'-methyl-2'-pyridyl)propyl]-3-allylamidinourea
1-[3-(3'-methyl-2'-pyridyl)propyl]-3-propargylamidinourea
1-[3-(3'-methyl-2'-pyridyl)propyl]-3-cyclopropylamidinourea
1-[3-(3'-methyl-2'-pyridyl)propyl]-3-methoxyethylamidinourea
1-[3-(3'-methyl-2'-pyridyl)propyl]-3-benzyloxyethylamidinourea
1-[3-(3'-methyl-2'-pyridyl)propyl]-3-phenethoxyethylamidinourea
1-[3-(3'-methyl-2'-pyridyl)propyl]-3-benzylamidinourea
1-[3-(3'-methyl-2'-pyridyl)propyl]-3-(N,N—dimethylamidino)urea
1-[3-(3'-methyl-2'-pyridyl)propyl]-3-(N,N—diethylamidino)urea
1-[3-(3'-methyl-2'-pyridyl)propyl]-3-(N,N—tetramethyleneamidino)urea
1-[3-(3'-methyl-2'-pyridyl)propyl] -3-(N,N—pentamethyleneamidino)urea
1-[3-(3'-chloro-2'-pyridyl)propyl]-3-methylamidinourea
1-[3-(3'-chloro-2'-pyridyl)propyl]-3-ethylamidinourea
1-[3-(3'-chloro-2'-pyridyl)propyl]-3-propylamidinourea
1-[3-(3'-chloro-2'-pyridyl)propyl]-3-i-propylamidinourea
1-[3-(3'-chloro-2'-pyridyl)propyl]-3-butylamidinourea
1-[3-(3'-chloro-2'-pyridyl)propyl]-3-i-butylamidinourea
1-[3-(3'-chloro-2'-pyridyl)propyl]-3-t-butylamidinourea
1-[3-(3'-chloro-2'-pyridyl)propyl]-3-pentylamidinourea
1-[3-(3'-chloro-2'-pyridyl)propyl]-3-allylamidinourea
1-[3-(3'-chloro-2'-pyridyl)propyl]-3-propargylamidinourea
1-[3-(3'-chloro-2'-pyridyl)propyl]-3-cyclopropylamidinourea
1-[3-(3'-chloro-2'-pyridyl)propyl]-3-cyclobutylamidinourea
1-[3-(3'-chloro-2'-pyridyl)propyl]-3-(N—[3'-cyclopentenyl]amidino)urea
1-[3-(3'-chloro-2'-pyridyl)propyl]-3-cyclopropylmethylamidinourea
1-[3-(3'-chloro-2'-pyridyl)propyl]-3-methoxyethylamidinourea
1-[3-(3'-chloro-2'-pyridyl)propyl]-3-benzyloxyethylamidinourea
1-[3-(3'-chloro-2'-pyridyl)propyl]-3-phenethoxyethylamidinourea
1-[3-(3'-chloro-2'-pyridyl)propyl]-3-benzylamidinourea
1-[3-(3'-chloro-2'-pyridyl)propyl]-3-(N,N—dimethylamidino)urea
1-[3-(3'-chloro-2'-pyridyl)propyl]-3-(N,N—diethylamidino)urea
1-[3-(3'-chloro-2'-pyridyl)propyl]-3-(N,N—tetramethylenamidino)urea
1-[3-(2'-pyridyl)propyl]-3-(N,N[3'-methyl-3'-azapentamethylene]amidino)urea
1-[3-(2'-pyridyl)propyl]-3-(N,N[3'-oxapentamethylene]amidino)urea

TABLE I-continued

1-[3-(2'-pyridyl)propyl]-3-methylamidinourea
1-[3-(2'-pyridyl)propyl]-3-ethylamidinourea
1-[3-(2'-pyridyl)propyl]-3-propylamidinourea
1-[3-(2'-pyridyl)propyl]-3-i-propylamidinourea
1-[3-(2'-pyridyl)propyl]-3-butylamidinourea
1-[3-(2'-pyridyl)propyl]-3-i-butylamidinourea
1-[3-(2'-pryidyl)propyl]-3-t-butylamidinourea
1-[3-(3'-pyridyl)propyl]-3-pentylamidinourea
1-[3-(3'-pyridyl)propyl]-3-allylamidinourea
1-[3-(3'-pyridyl)propyl]-3-propargylamidinourea
1-[3-(3'-pyridyl)propyl]-3-cyclobutylamidinourea
1-[3-(3'-pyridyl)propyl]-3-cyclohexylamidinourea
1-[3-(3'-pyridyl)propyl]-3-benzylamidinourea
1-[3-(3'-pyridyl)propyl]-3-methoxyethylamidinourea
1-[3-(3'-pyridyl)propyl]-3-benzyloxyethylamidinourea
1-[3-(3'-pyridyl)propyl]-3-methoxyethylamidinourea
1-[3-(3'-pyridyl)propyl]-3-benzyloxyethylamidinourea
1-[3-(3'-pyridyl)propyl]-3-phenethoxyethylamidinourea
1-[3-(3'-pyridyl)propyl]-3-(N,N—dimethylamidino)urea
1-[3-(3'-pyridyl)propyl]-3-(N,N—diethylamidino)urea
1-[3-(3'-pyridyl)propyl]-3-(N,N—pentamethyleneamidino)urea
1-[3-(4'-pyridyl)propyl]-3-methylamidinourea
1-[3-(4'-pyridyl)propyl]-3-ethylamidinourea
1-[3-(4'-pyridyl)propyl]-3-propylamidinourea
1-[3-(4'-pyridyl)propyl]-3-i-propylamidinourea
1-[3-(4'-pyridyl)propyl]-3-butylamidinourea
1-[3-(4'-pyridyl)propyl]-3-t-butylamidinourea
1-[3-(4'-pyridyl)propyl]-3-pentylamidinourea
1-[3-(4'-pyridyl)propyl]-3-hexylamidinourea
1-[3-(4'-pyridyl)propyl]-3-propargylamidinourea
1-[3-(4'-pyridyl)propyl]-3-allylamidinourea
1-[3-(4'-pyridyl)propyl]-3-methoxyethylamidinourea
1-[3-(4'-pyridyl)propyl]-3-benzyloxyethylamidinourea
1-[3-(4'-pyridyl)propyl]-3-phenethoxyethylamidinourea
1-[3-(4'-pyridyl)propyl]-3-(N,N—dimethylamidino)urea
1-[3-(4'-pyridyl)propyl]-3-(N,N—diethylamidino)urea
1-[3-(4'-pyridyl)propyl]-3-(N—methyl-N—ethylamidino)urea
1-[3-(3'-methyl-2'-pyridyl)propyl]-3-(N,N—tetramethyleneamidino)urea
1-[3-(3'-methyl-2'-pyridyl)propyl]-3-(N,N—pentamethyleneamidino)urea
1-[3-(3'-chloro-2'-pyridyl)propyl]-3-methylamidinourea
1-[3-(3'-chloro-2'-pyridyl)propyl]-3-ethylamidinourea
1-[3-(3'-chloro-2'-pyridyl)propyl]-3-propylamidinourea
1-[3-(3'-chloro-2'-pyridyl)propyl]-3-i-propylamidinourea
1-[3-(3'-chloro-2'-pyridyl)propyl]-3-butylamidinourea
1-[3-(3'-chloro-2'-pyridyl)propyl]-3-i-butylamidinourea
1-[3-(3'-chloro-2'-pyridyl)propyl]-3-t-butylamidinourea
1-[3-(3'-chloro-2'-pyridyl)propyl]-3-pentylamidinourea
1-[3-(3'-chloro-2'-pyridyl)propyl]-3-allylamidinourea
1-[3-(3'-chloro-2'-pyridyl)propyl]-3-propargylamidinourea
1-[3-(3'-chloro-2'-pyridyl)propyl]-3-cyclopropylamidinourea
1-[3-(3'-chloro-2'-pyridyl)propyl]-3-cyclobutylamidinourea
1-[3-(3'-chloro-2'-pyridyl)propyl]-3-(N—[3'-cyclopentenyl]amidino)urea
1-[3-(3'-chloro-2'-pyridyl)propyl]-3-cyclopropylmethylamidinourea
1-[3-(3'-chloro-2'-pyridyl)propyl]-3-methoxyethylamidinourea
1-[3-(3'-chloro-2'-pyridyl)propyl]-3-benzyloxyethylamidinourea
1-[3-(3'-chloro-2'-pyridyl)propyl]-3-phenethoxyethylamidinourea
1-[3-(3'-chloro-2'-pyridyl)propyl]-3-benzylamidinourea
1-[3-(3'-chloro-2'-pyridyl)propyl]-3-(N,N—dimethylamidino)urea
1-[3-(3'-chloro-2'-pyridyl)propyl]-3-(N,N—diethylamidino)urea
1-[3-(3'-chloro-2'-pyridyl)propyl]-3-(N,N—tetramethyleneamidino)urea
1-[3-(2'-pyridyl)propyl]-3-(N,N[3'-methyl-3'-azapentamethylene]amidino)urea
1-[3-(2'-pyridyl)propyl]-3-(N,N[3'-oxapentamethylene]amidino)urea
1-[3-(2'-pyridyl)propyl]-3-methylamidinourea
1-[3-(2'-pyridyl)propyl]-3-ethylamidinourea
1-[3-(2'-pyridyl)propyl]-3-propylamidinourea
1-[3-(2'-pyridyl)propyl]-3-i-propylamidinourea
1-[3-(2'-pyridyl)propyl]-3-butylamidinourea
1-[3-(2'-pyridyl)propyl]-3-i-butylamidinourea
1-[3-(3'-pyridyl)propyl]-3-t-butylamidinourea
1-[3-(3'-pyridyl)propyl]-3-pentylamidinourea
1-[3-(3'-pyridyl)propyl]-3-allylamidinourea
1-[3-(3'-pyridyl)propyl]-3-propargylamidinourea
1-[3-(3'-pyridyl)propyl]-3-cyclobutylamidinourea
1-[3-(3'-pyridyl)propyl]-3-cyclohexylamidinourea
1-[3-(3'-pyridyl)propyl]-3-benzylamidinourea
1-[3-(3'-pyridyl)propyl]-3-methoxyethylamidinourea
1-[3-(3'-pyridyl)propyl]-3-benzyloxyethylamidinourea
1-[3 (3'-pyridyl)propyl]-3-methoxyethylamidinourea
1-[3-(3'-pyridyl)propyl]-3-benzyloxyethylamidinourea
1-[3-(3'-pyridyl)propyl]-3-phenethoxyethylamidinourea
1-[3-(3'-pyridyl)propyl]-3-(N,N—dimethylamidino)urea
1-[3-(3'-pyridyl)propyl]-3-(N,N—diethylamidino)urea
1-[3-(3'-pyridyl)propyl]-3-(N,N—pentamethyleneamidino)urea
1-[3-(4'-pyridyl)propyl]-3-methylamidinourea
1-[3-(4'-pyridyl)propyl]-3-ethylamidinourea
1-[3-(4'-pyridyl)propyl]-3-propylamidinourea
1-[3-(4'-pyridyl)propyl]-3-i-propylamidinourea
1-[3-(4'-pyridyl)propyl]-3-butylamidinourea
1-[3-(4'-pyridyl)propyl]-3-t-butylamidinourea
1-[3-(4'-pyridyl)propyl]-3-pentylamidinourea
1-[3-(4'-pyridyl)propyl]-3-hexylamidinourea
1-[3-(4'-pyridyl)propyl]-3-propargylamidinourea
1-[3-(4'-pyridyl)propyl]-3-allylamidinourea
1-[3-(4'-pyridyl)propyl]-3-methoxyethylamidinourea
1-[3-(4'-pyridyl)propyl]-3-benzyloxyethylamidinourea
1-[3-(4'-pyridyl)propyl]-3-phenethoxyethylamidinourea
1-[3-(4'-pyridyl)propyl]-3-(N,N—dimethylamidino)urea
1-[3-(4'-pyridyl)propyl]-3-(N,N—diethylamidino)urea
1-[3-(4'-pyridyl)propyl]-3-(N—methyl-N—ethylamidino)urea
1-(2'-pyridylmethyl)-3-methylamidinothiourea
1-(2'-pyridylmethyl)-3-ethylamidinothiourea
1-(2'-pyridylmethyl)-3-propylamidinothiourea
1-(2'-pyridylmethyl)-3-i-propylamidinothiourea
1-(2'-pyridylmethyl)-3-butylamidinothiourea
1-(2'-pyridylmethyl)-3-i-butylamidinothiourea
1-(2'-pyridylmethyl)-3-pentylamidinothiourea
1-(2'-pyridylmethyl)-3-propargylamidinothiourea
1-(2'-pyridylmethyl)-3-allylamidinothiourea
1-(2'-pyridylmethyl)-3-methoxyethylamidinothiourea
1-(2'-pyridylmethyl)-3-benzyloxyethylamidinothiourea
1-(2'-pyridylmethyl)-3-phenethoxyethylamidinothiourea
1-(2'-pyridylmethyl)-3-(N,N—dimethylamidino)thiourea
1-(2'-pyridylmethyl)-3-(N,N—diethylamidino)thiourea
1-(2'-pyridylmethyl)-3-(N,N—tetramethyleneamidino)thiourea
1-(2'-pyridylmethyl)-3-(N,N—pentamethyleneamidino)thiourea
1-(2'-pyridylmethyl)-3-(N,N—hexamethyleneamidino)thiourea
1-(3'-methyl-2'-pyridylmethyl)-3-methylamidinothiourea
1-(3'-methyl-2'-pyridylmethyl)-3-ethylamidinothiourea
1-(3'-methyl-2'-pyridylmethyl)-3-propylamidinothiourea
1-(3'-methyl-2'-pyridylmethyl)-3-i-propylamidinothiourea
1-(3'-methyl-2'-pyridylmethyl)-3-i-butylamidinothiourea
1-(3'-methyl-2'-pyridylmethyl)-3-pentylamidinothiourea
1-(3'-methyl-2'-pyridylmethyl)-3-allylamidinothiourea
1-(3'-methyl-2'-pyridylmethyl)-3-propargylamidinothiourea
1-(3'-methyl-2'-pyridylmethyl)-3-cyclopropylamidinothiourea
1-(3'-methyl-2'-pyridylmethyl)-3-methoxyethylamidinothiourea
1-(3'-methyl-2'-pyridylmethyl)-3-benzyloxyethylamidinothiourea
1-(3'-methyl-2'pyridylmethyl)-3-phenethoxyethylamidinothiourea
1-(3'-methyl-2'-pyridylmethyl)-3-benzylamidinothiourea
1-(3'-methyl-2'-pyridylmethyl)-3-(N,N—dimethylamidino)thiourea
1-(3'-methyl-2'-pyridylmethyl)-3-(N,N—diethylamidino)thiourea
1-(3'-methyl-2'-pyridylmethyl)-3-(N,N—tetramethyleneamidino)thiourea
1-(3'-methyl-2'-pyridylmethyl)-3-(N,N—pentamethyleneamidino)thiourea
1-(3'-chloro-2'-pyridylmethyl)-3-methylamidinothiourea
1-(3'-chloro-2'-pyridylmethyl)-3-ethylamidinothiourea
1-(3'-chloro-2'-pyridylmethyl)-3-propylamidinothiourea
1-(3'-chloro-2'-pyridylmethyl)-3-i-propylamidinothiourea
1-(3'-chloro-2'-pyridylmethyl)-3-butylamidinothiourea
1-(3'-chloro 2'-pyridylmethyl)-3-i-butylamidinothiourea
1-(3'-chloro-2'-pyridylmethyl)-3-t-butylamidinothiourea
1-(3'-chloro-2'-pyridylmethyl)-3-pentylamidinothiourea
1-(3'-chloro-2'-pyridylmethyl)-3-allylamidinothiourea
1-(3'-chloro-2'-pyridylmethyl)-3-propargylamidinothiourea
1-(3'-chloro-2'-pyridylmethyl)-3-cyclopropylamidinothiourea
1-(3'-chloro-2'-pyridylmethyl)-3-cyclobutylamidinothiourea
1-(3'-chloro-2'-pyridylmethyl)-3-(N—[3'-cyclopentenyl]amidino)thiourea
1-(3'-chloro-2'-pyridylmethyl)-3-cyclopropylmethylamidinothiourea
1-(3'-chloro-2'-pyridylmethyl)-3-methoxyethylamidinothiourea
1-(3'-chloro-2'-pyridylmethyl)-3-benzyloxyethylamidinothiourea
1-(3'-chloro-2'-pyridylmethyl)-3-phenethoxyethylamidinothiourea
1-(3'-chloro-2'-pyridylmethyl)-3-benzylamidinothiourea
1-(3'-chloro-2'-pyridylmethyl)-3-(N,N—dimethylamidino)thiourea
1-(3'-chloro-2'-pyridylmethyl)-3-(N,N—diethylamidino)thiourea
1-(3'-chloro-2'-pyridylmethyl)-3-(N,N—tetramethyleneamidino)thiourea
1-(2'-pyridylmethyl)-3-(N,N[3'-methyl-3'-

TABLE I-continued azapentamethylene]amidino)thiourea
1-(2'-pyridylmethyl)-3-(N,N[3'-oxapentamethylene]amidino)thiourea
1-(2'-pyridylmethyl)-3-methylamidinothiourea
1-(2'-pyridylmethyl)-3-ethylamidinothiourea
1-(2'-pyridylmethyl)-3-propylamidinothiourea
1-(2'-pyridylmethyl)-3-i-propylamidinothiourea
1-(2'-pyridylmethyl)-3-butylamidinothiourea
1-(2'-pyridylmethyl)-3-i-butylamidinothiourea
1-(3'-pyridylmethyl)-3-t-butylamidinothiourea
1-(3'-pyridylmethyl)-3-pentylamidinothiourea
1-(3'-pyridylmethyl)-3-allylamidinothiourea
1-(3'-pyridylmethyl)-3-propargylamidinothiourea
1-(3'-pyridylmethyl)-3-cyclobutylamidinothiourea
1-(3'-pyridylmethyl)-3-cyclohexylamidinothiourea
1-(3'-pyridylmethyl)-3-benzylamidinothiourea
1-(3'-pyridylmethyl)-3-methoxyethylamidinothiourea
1-(3'-pyridylmethyl)-3-benzyloxyethylamidinothiourea
1-(3'-pyridylmethyl)-3-methoxyethylamidinothiourea
1-(3'-pyridylmethyl)-3-benzyloxyethylamidinothiourea
1-(3'-pyridylmethyl)-3-phenethoxyethylamidinothiourea
1-(3'-pyridylmethyl)-3-(N,N—dimethylamidino)thiourea
1-(3'-pyridylmethyl)-3-(N,N—diethylamidino)thiourea
1-(3'-pyridylmethyl)-3-(N,N—pentamethyleneamidino)thiourea
1-(4'-pyridylmethyl)-3-methylamidinothiourea
1-(4'-pyridylmethyl)-3-ethylamidinothiourea
1-(4'-pyridylmethyl)-3-propylamidinothiourea
1-(4'-pyridylmethyl)-3-i-propylamidinothiourea
1-(4'-pyridylmethyl)-3-butylamidinothiourea
1-(4'-pyridylmethyl)-3-t-butylamidinothiourea
1-(4'-pyridylmethyl)-3-pentylamidinothiourea
1-(4'-pyridylmethyl)-3-hexylamidinothiourea
1-(4'-pyridylmethyl)-3-propargylamidinothiourea
1-(4'-pyridylmethyl)-3-allylamidinothiourea
1-(4'-pyridylmethyl)-3-methoxyethylamidinothiourea
1-(4'-pyridylmethyl)-3-benzyloxyethylamidinothiourea
1-(4'-pyridylmethyl)-3-phenethoxyethylamidinothiourea
1-(4'-pyridylmethyl)-3-(N,N—dimethylamidino)thiourea
1-(4'-pyridylmethyl)-3-(N,N—diethylamidino)thiourea
1-(4'-pyridylmethyl)-3-(N—methyl-N—ethylamidino)thiourea
1-[2-(2'-pyridyl)ethyl]-3-methylamidinothiourea
1-[2-(2'-pyridyl)ethyl]-3-ethylamidinothiourea
1-[2-(2'-pyridyl)ethyl]-3-propylamidinothiourea
1-[2-(2'-pyridyl)ethyl]-3-i-propylamidinothiourea
1-[2-(2'-pyridyl)ethyl]-3-butylamidinothiourea
1-[2-(2'-pyridyl)ethyl]-3-i-butylamidinothiourea
1-[2-(2'-pyridyl)ethyl]-3-pentylamidinothiourea
1-[2-(2'-pyridyl)ethyl]-3-propargylamidinothiourea
1-[2-(2'-pyridyl)ethyl]-3-allylamidinothiourea
1-[2-(2'-pyridyl)ethyl]-3-methoxyethylamidinothiourea
1-[2-(2'-pyridyl)ethyl]-3-benzyloxyethylamidinothiourea
1-[2-(2'-pyridyl)ethyl]-3-phenethoxyethylamidinothiourea
1-[2-(2'-pyridyl)ethyl]-3-(N,N—dimethylamidino)thiourea
1-[2-(2'-pyridyl)ethyl]-3-(N,N—diethylamidino)thiourea
1-[2-(2'-pyridyl)ethyl]-3-(N,N—tetramethyleneamidino)thiourea
1-[2-(2'-pyridyl)ethyl]-3-(N,N—pentamethyleneamidino)thiourea
1-[2-(2'-pyridyl)ethyl]-3-(N,N—hexamethyleneamidino)thiourea
1-[2-(3'-methyl-2'-pyridyl)ethyl]-3-methylamidinothiourea
1-[2-(3'-methyl-2'-pyridyl)ethyl]-3-ethylamidinothiourea
1-[2-(3'-methyl-2'-pyridyl)ethyl]-3-propylamidinothiourea
1-[2-(3'-methyl-2'-pyridyl)ethyl]-3-i-propylamidinothiourea
1-[2-(3'-methyl-2'-pyridyl)ethyl]-3-i-butylamidinothiourea
1-[2-(3'-methyl-2'-pyridyl)ethyl]-3-pentylamidinothiourea
1-[2-(3'-methyl-2'-pyridyl)ethyl]-3-allylamidinothiourea
1-[2-(3'-methyl-2'-pyridyl)ethyl]-3-propargylamidinothiourea
1-[2-(3'-methyl-2'-pyridyl)ethyl]-3-cyclopropylamidinothiourea
1-[2-(3'-methyl-2'-pyridyl)ethyl]-3-methoxyethylamidinothiourea
1-[2-(3'-methyl-2'-pyridyl)ethyl]-3-benzyloxyethylamidinothiourea
1-[2-(3'-methyl-2'-pyridyl)ethyl]-3-phenethoxyethylamidinothiourea
1-[2-(3'-methyl-2'-pyridyl)ethyl]-3-benzylamidinothiourea
1-[2-(3'-methyl-2'-pyridyl)ethyl]-3-(N,N—dimethylamidino)thiourea
1-[2-(3'-methyl-2'-pyridyl)ethyl]-3-(N,N—diethylamidino)thiourea
1-[2-(3'-methyl-2'-pyridyl)ethyl]-3-(N,N—tetramethyleneamidino)thiourea
1-[2-(3'-methyl-2'-pyridyl)ethyl]-3-N,N—pentamethyleneamidino)thiourea
1-[2-(3'-chloro-2'-pyridyl)ethyl]-3-methylamidinothiourea
1-[2-(3'-chloro-2'-pyridyl)ethyl]-3-ethylamidinothiourea
1-[2-(3'-chloro-2'-pyridyl)ethyl]-3-propylamidinothiourea
1-[2-(3'-chloro-2'-pyridyl)ethyl]-3-i-propylamidinothiourea
1-[2-(3'-chloro-2'-pyridyl)ethyl]-3-butylamidinothiourea
1-[2-(3'-chloro-2'-pyridyl)ethyl]-3-i-butylamidinothiourea
1-[2-(3'-chloro-2'-pyridyl)ethyl]-3-t-butylamidinothiourea
1-[2-(3'-chloro-2'-pyridyl)ethyl]-3-pentylamidinothiourea
1-[2-(3'-chloro-2'-pyridyl)ethyl]-3-allylamidinothiourea
1-[2-(3'-chloro-2'-pyridyl)ethyl]-3-propargylamidinothiourea
1-[2-(3'-chloro-2'-pyridyl)ethyl]-3-cyclopropylamidinothiourea
1-[2-(3'-chloro-2'-pyridyl)ethyl]-3-cyclobutylamidinothiourea
1-[2-(3'-chloro-2'-pyridyl)ethyl]-3-(N—[3'-cyclopentenyl]amidino)thiourea
1-[2-(3'-chloro-2'-pyridyl)ethyl]-3-cyclopropylmethylamidinothiourea
1-[2-(3'-chloro-2'-pyridyl)ethyl]-3-methoxyethylamidinothiourea
1-[2-(3'-chloro-2'-pyridyl)ethyl]-3-benzyloxyethylamidinothiourea
1-[2-(3'-chloro-2'-pyridyl)ethyl]-3-phenethoxyethylamidinothiourea
1-[2-(3'-chloro-2'-pyridyl)ethyl]-3-benzylamidinothiourea
1-[2-(3'-chloro-2'-pyridyl)ethyl]-3-(N,N—dimethylamidino)thiourea
1-[2-(3'-chloro-2'-pyridyl)ethyl]-3-(N,N—diethylamidino)thiourea
1-[2-(3'-chloro-2'-pyridyl)ethyl]-3-(N,N—tetramethyleneamidino)thiourea
1-[2-(2'-pyridyl)ethyl]-3-(N,N[3'-methyl-3'-azapentamethylene]amidino)thiourea
1-[2-(2'-pyridyl)ethyl]-3-(N,N[3'-oxapentamethylene]amidino]thiourea
1-[2-(2'-pyridyl)ethyl]-3-methylamidinothiourea
1-[2-(2'-pyridyl)ethyl]-3-ethylamidinothirea
1-[2-(2'-pyridyl)ethyl]-3-propylamidinothiourea
1-[2-(2'-pyridyl)ethyl]-3-i-propylamidinothiourea
1-[2-(2'-pyridyl)ethyl]-3-butylamidinothiourea
1-[2-(2'-pyridyl)ethyl]-3-i-butylamidinothiourea
1-[2-(3'-pyridyl)ethyl]-3-butylamidinothiourea
1-[2-(3'-pyridyl)ethyl]-3-pentylamidinothiourea
1-[2-(3'-pyridyl)ethyl]-3-allylamidinothiourea
1-[2-(3'-pyridyl)ethyl]-3-propargylamidinothiourea
1-[2-(3'-pyridyl)ethyl]-3-cyclobutylamidinothiourea
1-[2-(3'-pyridyl)ethyl]-3-cyclohexylamidinothiourea
1-[2-(3'-pyridyl)ethyl]-3-benzylamidinothiourea
1-[2-(3'-pyridyl)ethyl]-3-methoxyethylamidinothiourea
1-[2-(3'-pyridyl)ethyl]-3-benzyloxyethylamidinothiourea
1-[2-(3'-pyridyl)ethyl]-3-methoxyethylamidinothiourea
1-[2-(3'-pyridyl)ethyl]-3-benzyloxyethylamidinothiourea
1-[2-(3'-pyridyl)ethyl]-3-phenethoxyethylamidinothiourea
1-[2-(3'-pyridyl)ethyl]-3-(N,N—dimethylamidino)thiourea
1-[2-(3'-pyridyl)ethyl]-3-(N,N—diethylamidino)thiourea
1-[2-(3'-pyridyl)ethyl]-3-(N,N—pentamethyleneamidino)thiourea
1-[2-(4'-pyridyl)ethyl]-3-methylamidinothiourea
1-[2-(4'-pyridyl)ethyl]-3-ethylamidinothiourea
1-[2-(4'-pyridyl)ethyl]-3-propylamidinothiourea
1-[2-(4'-pyridyl)ethyl]-3-i-propylamidinothiourea
1-[2-(4'-pyridyl)ethyl]-3-butylamidinothiourea
1-[2-(4'-pyridyl)ethyl]-3-t-butylamidinothiourea
1-[2-(4'-pyridyl)ethyl]-3-pentylamidinothiourea
1-[2-(4'-pyridyl)ethyl]-3-hexylamidinothiourea
1-[2-(4'-pyridyl)ethyl]-3-propargylamidinothiourea
1-[2-(4'-pyridyl)ethyl]-3-allylamidinothiourea
1-[2-(4'-pyridyl)ethyl]-3-methoxyethylamidinothiourea
1-[2-(4'-pyridyl)ethyl]-3-benzyloxyethylamidinothiourea
1-[2-(4'-pyridyl)ethyl]-3-phenethoxyethylamidinothiourea
1-[2-(4'-pyridyl)ethyl]-3-(N,N—dimethylamidino)thiourea
1-[2-(4'-pyrldyl)ethyl]-3-(N,N—diethylamidino)thiourea
1-[2-(4'-pyridyl)ethyl]-3-(N—methyl-N—ethylamidino)thiourea
1-[3-(2'-pyridyl)propyl]-3-methylamidinothiourea
1-[3-(2'-pyridyl)propyl]-3-ethylamidinothiourea
1-[3-(2'-pyridyl)propyl] -3-propylamidinothiourea
1-[3-(2'-pyridyl)propyl]-3-i-propylamidinothiourea
1-[3-(2'-pyridyl)propyl]-3-butylamidinothiourea
1-[3-(2'-pyridyl)propyl]-3-i-butylamidinothiourea
1-[3-(2'-pyridyl)propyl]-3-pentylamidinothiourea
1-[3-(2'-pyridyl)propyl]-3-propargylamidinothiourea
1-[3-(2'-pyridyl)propyl]-3-allylamidinothiourea
1-[3-(2'-pyridyl)propyl]-3-methoxyethylamidinothiourea
1-[3-(2'-pyridyl)propyl]-3-benzyloxyethylamidinothiourea
1-[3-(2'-pyridyl)propyl]-3-phenethoxyethylamidinothiourea
1-[3-(2'-pyridyl)propyl]-3-(N,N—dimethylamidino)thiourea
1-[3-(2'-pyridyl)propyl]-3-(N,N—diethylamidino)thiourea
1-[3-(2'-pyridyl)propyl]-3-(N,N—tetramethyleneamidino)thiourea
1-[3-(2'-pyridyl)propyl]-3-(N,N—pentamethyleneamidino)thiourea
1-[3-(2'-pyridyl)propyl]-3-(N,N—hexamethyleneamidino)thiourea
1-[3-(3'-methyl-2'-pyridyl)propyl]-3-methylamidinothiourea
1-[3-(3'-methyl-2'-pyridyl)propyl]-3-ethylamidinothiourea
1-[3-(3'-methyl-2'-pyridyl)propyl]-3-propylamidinothiourea
1-[3-(3'-methyl-2'-pyridyl)propyl]-3-i-propylamidinothiourea
1-[3-(3'-methy1-2'-pyridyl)propyl]-3-i-butylamidinothiourea
1-[3-(3'-methyl-2'-pyridyl)propyl]-3-pentylamidinothiourea
1-[3-(3'-methyl-2'-pyridyl)propyl]-3-allylamidinothiourea

TABLE I-continued

1-[3-(3'-methyl-2'-pyridyl)propyl]-3-propargylamidinothiourea
1-[3-(3'-methyl-2'-pyridyl)propyl]-3-cyclopropylamidinothiourea
1-[3-(3'-methyl-2'-pyridyl)propyl]-3-methoxyethylamidinothiourea
1-[3-(3'-methyl-2'-pyridyl)propyl]-3-benzyloxyethylamidinothiourea
1-[3-(3'-methyl-2'-pyridyl)propyl]-3-phenethoxyethylamidinothiourea
1-[3-(3'-methyl-2'-pyridyl)propyl]-3-benzylamidinothiourea
1-[3-(3'-methyl-2'-pyridyl)propyl]-3-(N,N—dimethylamidino)thiourea
1-[3-(3'-methyl-2'-pyridyl)propyl]-3-(N,N—diethylamidino)thiourea
1-[3-(3'-methyl-2'-pyridyl)propyl]-3-(N,N—tetramethyleneamidino)thiourea
1-[3-(3'-methyl-2'-pyridyl)propyl]-3-(N,N—pentamethyleneamidino)thiourea
1-[3-(3'-chloro-2'-pyridyl)propyl]-3-methylamidinothiourea
1-[3-(3'-chloro-2'-pyridyl)propyl]-3-ethylamidinothiourea
1-[3-(3'-chloro-2'-pyridyl)propyl]-3-propylamidinothiourea
1-[3-(3'-chloro-2'-pyridyl)propyl]-3-i-propylamidinothiourea
1-[3-(3'-chloro-2'-pyridyl)propyl]-3-butylamidinothiourea
1-[3-(3'-chloro-2'-pyridyl)propyl]-3-i-butylamidinothiourea
1-[3-(3'-chloro-2'-pyridyl)propyl]-3-t-butylamidinothiourea
1-[3-(3'-chloro-2'-pyridyl)propyl]-3-pentylamidinothiourea
1-[3-(3'-chloro-2'-pyridyl)propyl]-3-allylamidinothiourea
1-[3-(3'-chloro-2'-pyridyl)propyl]-3-propargylamidinothiourea
1-[3-(3'-chloro-2'-pyridyl)propyl]-3-cyclopropylamidinothiourea
1-[3-(3'-chloro-2'-pyridyl)propyl]-3-cyclobutylamidinothiourea
1-[3-(3'-chloro-2'-pyridyl)propyl]-3-(N—[3'-cyclopentenyl]amidino)thiourea
1-[3-(3'-chloro-2'-pyridyl)propyl]-3-cyclopropylmethylamidinothiourea
1-[3-(3'-chloro-2'-pyridyl)propyl]-3-methoxyethylamidinothiourea
1-[3-(3'-chloro-2'-pyridyl)propyl]-3-benzyloxyethylamidinothiourea
1-[3-(3'-chloro-2'-pyridyl)propyl]-3-phenethoxyethylamidinothiourea
1-[3-(3'-chloro-2'-pyridyl)propyl]-3-benzylamidinothiourea
1-[3-(3'-chloro-2'-pyridyl)propyl]-3-(N,N—dimethylamidino)thiourea
1-[3-(3'-chloro-2'-pyridyl)propyl]-3-(N,N—diethylamidino)thiourea
1-[3-(3'-chloro-2'-pyridyl)propyl]-3-(N,N—tetramethyleneamidino)thiourea
1-[3-(2'-pyridyl)propyl]-3-(N,N[3'-methyl-3'-azapentamethylene]amidino)thiourea
1-[3-(2'-pyridyl)propyl]-3-(N,N[3'-oxapentamethylene]amidino)thiourea
1-[3-(2'-pyridyl)propyl]-3-methylamidinothiourea
1-[3-(2'-pyridyl)propyl]-3-ethylamidinothiourea
1-[3-(2'-pyridyl)propyl]-3-propylamidinothiourea
1-[3-(2'-pyridyl)propyl]-3-i-propylamidinothiourea
1-[3-(2'-pyridyl)propyl]-3-butylamidinothiourea
1-[3-(2'-pyridyl)propyl]-3-i-butylamidinothiourea
1-[3-(3'-pyridyl)propyl]-3-t-butylamidinothiourea
1-[3-(3'-pyridyl)propyl]-3-pentylamidinothiourea
1-[3-(3'-pyridyl)propyl]-3-allylamidinothiourea
1-[3-(3'-pyridyl)propyl]-3-propargylamidinothiourea
1-[3-(3'-pyridyl)propyl]-3-cyclobutylamidinothiourea
1-[3-(3'-pyridyl)propyl]-3-cyclohexylamidinothiourea
1-[3-(3'-pyridyl)propyl]-3-benzylamidinothiourea
1-[3-(3'-pyridyl)propyl]-3-methoxyethylamidinothiourea
1-[3-(3'-pyridyl)propyl]-3-benzyloxyethylamidinothiourea
1-[3-(3'-pyridyl)propyl]-3-methoxyethylamidinothiourea
1-[3-(3'-pyridyl)propyl]-3-benzyloxyethylamidinothiourea
1-[3-(3'-pyridyl)propyl]-3-phenethoxyethylamidinothiourea
1-[3-(3'-pyridyl)propyl]-3-(N,N—dimethylamidino)thiourea
1-[3-(3'-pyridyl)propyl]-3-(N,N—diethylamidino)thiourea
1-[3-(3'-pyridyl)propyl]-3-(N,N—pentamethyleneamidino)thiourea
1-[3-(4'-pyridyl)propyl]-3-methylamidinothiourea
1-[3-(4'-pyridyl)propyl]-3-ethylamidinothiourea
1-[3-(4'-pyridyl)propyl]-3-propylamidinothiourea
1-[3-(4'-pyridyl)propyl]-3-i-propylamidinothiourea
1-[3-(4'-pyridyl)propyl]-3-butylamidinothiourea
1-[3-(4'-pyridyl)propyl]-3-t-butylamidinothiourea
1-[3-(4'-pyridyl)propyl]-3-pentylamidinothiourea
1-[3-(4'-pyridyl)propyl]-3-hexylamidinothiourea
1-[3-(4'-pyridyl)propyl]-3-propargylamidinothiourea
1-[3-(4'-pyridyl)propyl]-3-allylamidinothiourea
1-[3-(4'-pyridyl)propyl]-3-methoxyethylamidinothiourea
1-[3-(4'-pyridyl)propyl]-3-benzyloxyethylamidinothiourea
1-[3-(4'-pyridyl)propyl]-3-phenethoxyethylamidinothiourea
1-[3-(4'-pyridyl)propyl]-3-(N,N—dimethylamidino)thiourea
1-[3-(4'-pyridyl)propyl]-3-(N,N—diethylamidino)thiourea
1-[3-(4'-pyridyl)propyl]-3-(N—methyl-N—ethylamidino)thiourea

TABLE II $$R_1-NB-\overset{X}{\underset{H}{\overset{\|}{C}}}-NH-\overset{NH}{\overset{\|}{C}}-N\overset{R_3}{\underset{R_4}{}}$$

X=S, O

| $R_1$ | $R_3$ | $R_4$ |
|---|---|---|
| 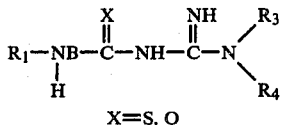 | H | H |
| 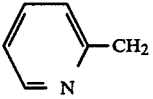 | H | —CH$_3$ |
| 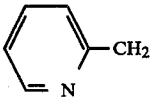 | H | —C$_2$H$_5$ |
| 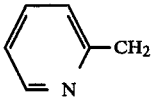 | —CH$_3$ | —CH$_3$ |
| 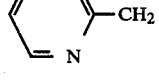 | H | —OCH$_3$ |
| 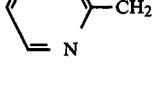 | H | —CH$_3$ |
| 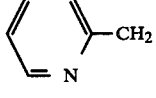 | —CH$_3$ | —CH$_3$ |
| 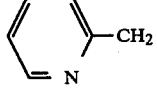 | —C$_2$H$_5$ | —C$_2$H$_5$ |
| 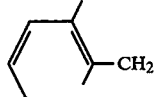 | H | H |
| 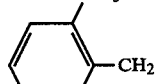 | H | —CH$_3$ |

TABLE II-continued
$$R_1-NB-\overset{X}{\underset{H}{C}}-NH-\overset{NH}{\underset{}{C}}-N\overset{R_3}{\underset{R_4}{}}$$
X=S, O
| $R_1$ | $R_3$ | $R_4$ |
|---|---|---|
| 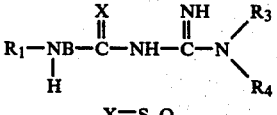 | H | —$C_2H_5$ |
| 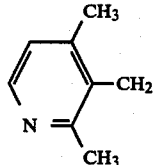 | H | —$OCH_3$ |
| 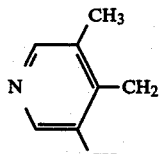 | —$CH_3$ | —$CH_3$ |
| 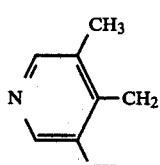 | —$CH_3$ | —$C_2H_5$ |
| 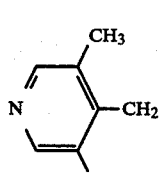 | H | H |
| 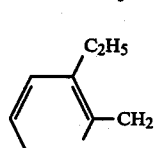 | H | —$CH_3$ |
| 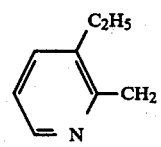 | H | —$C_2H_5$ |
| 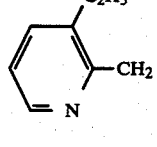 | H | —$CH_3$ |
| 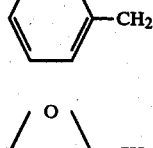 | H | H |
|  | H | —$CH_3$ |
| 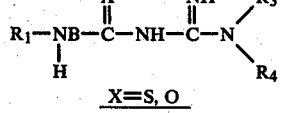 | H | —$C_2H_5$ |
| 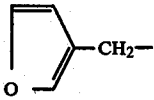 | —$CH_3$ | —$CH_3$ |
| 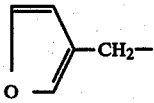 | —H | —$CH_3$ |
| 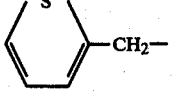 | —H | —$C_2H_5$ |
| 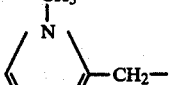 | —H | —$CH_3$ |
| 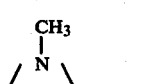 | H | —$CH_3$ |
| 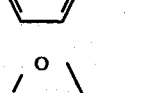 | H | —$CH_2H_5$ |
| 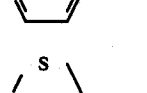 | H | —$CH_3$ |
| 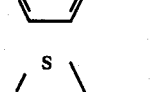 | H | H |
| 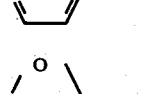 | H | —$CH_3$ |
| 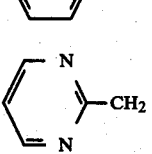 | —$CH_3$ | —$CH_3$ |

TABLE II-continued $$R_1-NB(H)-\overset{X}{C}-NH-\overset{NH}{C}-N(R_3)(R_4)$$

X=S, O

| $R_1$ | $R_3$ | $R_4$ |
|---|---|---|
| 2-pyrimidinyl-CH$_2$ | —H | —CH$_3$ |
| 2-pyrimidinyl-CH$_2$ | —H | —C$_2$H$_5$ |
| 2-pyrimidinyl-CH$_2$ | —CH$_3$ | —CH$_3$ |
| 4,6-dimethyl-5-pyrimidinyl-CH$_2$ | H | H |
| 4,6-dimethyl-5-pyrimidinyl-CH$_2$ | H | —CH$_3$ |
| 4,6-dimethyl-5-pyrimidinyl-CH$_2$ | —CH$_3$ | —CH$_3$ |
| 4,6-dimethyl-5-pyrimidinyl-CH$_2$ | H | —C$_2$H$_5$ |
| 4-pyridinyl-CH$_2$ | H | H |
| 4-pyridinyl-CH$_2$ | H | —CH$_3$ |
| imidazolyl-CH$_2$ (2-) | H | H |
| imidazolyl-CH$_2$ (2-) | H | —CH$_3$ |
| imidazolyl-CH$_2$ (2-) | H | —C$_2$H$_5$ |
| imidazolyl-CH$_2$ (5-) | H | H |
| imidazolyl-CH$_2$ (5-) | H | —CH$_3$ |
| 2-pyridinyl-CH$_2$CH$_2$— | H | H |
| 2-pyridinyl-CH$_2$CH$_2$— | H | —CH$_3$ |
| 2-pyridinyl-CH$_2$CH$_2$— | H | —C$_2$H$_5$ |
| 2-pyridinyl-CH$_2$CH$_2$— | —CH$_3$ | —CH$_3$ |
| 2-pyridinyl-CH$_2$CH$_2$— | H | —OCH$_3$ |
| 3-methyl-2-pyridinyl-CH$_2$CH$_2$— | H | —CH$_3$ |
| 3-methyl-2-pyridinyl-CH$_2$CH$_2$— | —CH$_3$ | —CH$_3$ |

TABLE II-continued

R₁—NB—C(=X)—NH—C(=NH)—N(R₃)(R₄) (with H on NB)

X = S, O

| R₁ | R₃ | R₄ |
|---|---|---|
| 3-methyl-2-(CH₂CH₂—)pyridine | —C₂H₅ | —C₂H₅ |
| 2,4-dimethyl-3-(CH₂CH₂—)pyridine | H | H |
| 2,4-dimethyl-3-(CH₂CH₂—)pyridine | H | —CH₃ |
| 2,4-dimethyl-3-(CH₂CH₂—)pyridine | H | —C₂H₅ |
| 3,5-dimethyl-4-(CH₂CH₂—)pyridine | H | —OCH₃ |
| 2,4-dimethyl-3-(CH₂CH₂—)pyridine | —CH₃ | —CH₃ |
| 2,4-dimethyl-3-(CH₂CH₂—)pyridine | —CH₃ | —C₂H₅ |
| 3-ethyl-2-(CH₂CH₂—)pyridine | H | H |
| 3-ethyl-2-(CH₂CH₂—)pyridine | H | —CH₃ |
| 3-ethyl-2-(CH₂CH₂—)pyridine | H | —C₂H₅ |
| 4,6-dimethyl-5-(CH₂CH₂—)pyrimidine | —CH₃ | —CH₃ |
| 4,6-dimethyl-5-(CH₂CH₂—)pyrimidine | H | —C₂H₅ |
| 4-(CH₂CH₂—)pyridine | H | H |
| 4-(CH₂CH₂—)pyridine | H | —CH₃ |
| 2-(CH₂CH₂—)imidazole | H | H |
| 2-(CH₂CH₂—)imidazole | H | —CH₃ |
| 2-(CH₂CH₂—)imidazole | H | —C₂H₅ |
| 5-(CH₂CH₂—)imidazole | H | H |

TABLE II-continued $$R_1-NB-\underset{H}{\overset{\overset{X}{\|}}{C}}-NH-\underset{}{\overset{\overset{NH}{\|}}{C}}-N\underset{R_4}{\overset{R_3}{\diagup}}$$

X=S, O

| R$_1$ | R$_3$ | R$_4$ |
|---|---|---|
| imidazolyl-CH$_2$CH$_2$– | H | –CH$_3$ |
| pyrazinyl-CH$_2$CH$_2$– | H | H |
| pyrazinyl-CH$_2$CH$_2$– | H | –CH$_3$ |
| pyrazinyl-CH$_2$CH$_2$– | –CH$_3$ | –CH$_3$ |
| pyrazinyl-CH$_2$CH$_2$– | –H | –CH$_3$ |
| pyrazinyl-CH$_2$CH$_2$– | –H | –C$_2$H$_5$ |
| pyrazinyl-CH$_2$CH$_2$– | –CH$_3$ | –CH$_3$ |
| dimethylpyrimidinyl-CH$_2$– | H | H |
| dimethylpyrimidinyl-CH$_2$– | H | –CH$_3$ |
| pyranyl-CH$_2$CH$_2$– | H | –CH$_3$ |
| pyranyl-CH$_2$-CH$_2$– | H | H |
| furanyl-CH$_2$-CH$_2$– | H | –CH$_3$ |
| furanyl-CH$_2$-CH$_2$– | H | –C$_2$H$_5$ |
| thiopyranyl-CH$_2$-CH$_2$– | –CH$_3$ | –CH$_3$ |
| N-methylpyridinyl-CH$_2$-CH$_2$– | –H | –CH$_3$ |
| N-methylpyridinyl-CH$_2$-CH$_2$– | –H | –C$_2$H$_5$ |
| isoxazolyl-CH$_2$-CH$_2$– | –H | –CH$_3$ |
| thiazolyl-CH$_2$CH$_2$– | H | –CH$_3$ |
| thiazolyl-CH$_2$CH$_2$– | H | –CH$_2$H$_5$ |
| isoxazolyl-CH$_2$CH$_2$– | H | –CH$_3$ |

The compounds of this invention may be prepared by the following general synthesis.

Condensation of a heterocyclic alkylene isocyanate (or isothiocyanate), prepared from the heterocyclic alkylene amine and phosgene or thiophosgene in the customary manner, with an appropriate substituted guanidine results in a 1-heterocyclicalkylene-3-substituted amidinourea (or thiourea). The reaction is carried out in a polar media using solvents such as alcohol, tetrahydrofuran, etc. It is convenient to carry out the reaction by preparing the isocyanate in the reaction media and then forming a guanidine in situ by hydrolyzing a guanidine carbonate with base. Condensation of the isocyanate takes place when the guanidine forms and the amidinourea compounds result.

When $R_2$ substitution is desired the starting material can be a heterocyclic alkylene N-alkylamine. Reaction with phosgene (or thiophosgene) results in the heterocyclic acid chloride (or thioacid chloride) which is then reacted with the appropriate substituted guanidine to prepare the amidinourea or amidinothiourea. (Scheme I)

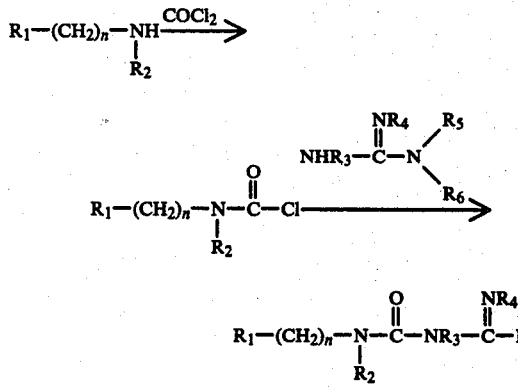

Another method of preparing $R_2$ substituted amidinothioureas is one in which the heterocyclic alkylene N-alkylamine is reacted with ammonium or sodium thiocyanate to form a thiourea. Subsequent reaction with an appropriate substituted cyanamide forms the heterocyclic alkylene $R_2$ substituted amidinourea. (Scheme II)

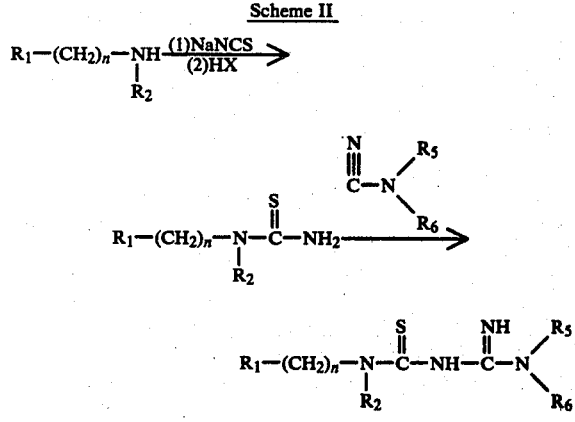

Another method for preparing heterocyclic alkylene amidinoureas is by reacting a phenyl carbamate with an appropriately substituted guanidine. The reaction may be conducted in a polar aprotic solvent. It is preferred to hydrolyze the guanidine sulfate in situ and react it with the carbamate. (Scheme III)

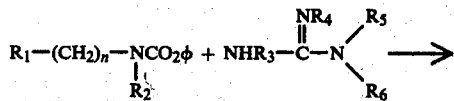

-continued
Scheme III

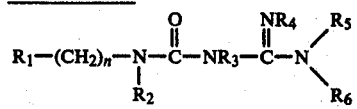

The starting heterocyclic alkylene amines are known, or may be prepared by known techniques.

Reactions may also be carried out at other stages of synthesis depending on the substituents present and the substituents desired. Various combinations of the foregoing reactions will be determined by one skilled in the art in order that the desired product results. Thus a pyridylmethylene amidinourea may be halogenated or nitrated, etc.

The following are detailed examples which show the synthetic preparation of the compounds of this invention.

EXAMPLE 1

Preparation of 1-propylamidino-3-(2-pyridylmethyl)urea 75.10 g (0.25 moles) of propylguanidine sulfate are added to a stirred mixture of 40 g of a 50% aqueous NaOH and 500 ml of THF. After stirring at RT for two hours, 75 g of anhydrous $Na_2SO_4$ are added. Stirring is continued for one hour. A solution of 57.06 g (0.25 mol) of O'-phenyl-N-(2-pyridylmethyl) carbamate in 100 ml of $CH_2Cl_2$ is added rapidly in small portions to the stirred mixture. The reaction is warmed to near boiling for one hour. The mixture is allowed to stand at room temperature overnight. The product is extracted with $CH_2Cl_2$, dried (sat'd NaCl), concentrated and recrystallized from boiling $CH_3CN$ to give 18.89 g (28%) of 1-n-propylamidino-3-(2-pyridylmethyl)urea, M.P. 195°–197° C.

EXAMPLE 2

Preparation of 1-methylamidino-3-[2-(2'-pyridyl)ethyl]thiourea 9.6 g (0.12 moles) of 50% w/w aqueous NaOH are added dropwise to a stirred suspension of 17.7 g (60.0 mmol) of methylguanidine sulfate in 200 ml of the THF. The mixture is stirred for one hour after which 10.0 g of anhydrous $NaSO_4$ are added and stirring continued for an additional half hour. Over a period of one to two hours, a solution of 10.0 g of 2-(2-pyridyl)ethylisothiocyanate in 100 ml of a 9 to 1 THF/MeOH mixture is added dropwise and the reaction stirred overnight. The THF is evaporated and the residue partitioned between $H_2O$ and $CHCl_3$. The aqueous layer is extracted with $CHCl_3$, dried and concentrated to give a dark oil. The oil is dissolved in EtOAc and placed on a silica gel column to give a yellow-orange solid which is twice recrystallized from $CH_3CN$ to give 2.0 g (14%) of 1-methylamidino-3-[2'-pyridyl)ethyl]thiourea as an orange solid.

This invention further describes a novel method for the treatment of human and veterinary spasmolytic disorders, arrhythmic conditions, hypertensive conditions, gastrointestinal disorders and protozoal infestations by the administration of a compound of the Formula I.

The compounds of this invention have a useful degree of gastric antisecretory activty and are effective in reducing the volume and the acidity of the gastric fluid in humans and mammals. Further, these compounds produce a considerable spasmolytic action on the gastrointestinal musculature, i.e., they reduce the peristaltic action of the gastrointestinal musculature which is manifested by a delay in gastric emptying time. It should further be noted that these compounds are also characterized by their low acute oral toxicity.

In particular, the heterocyclic alklene amidinoureas as herein described are useful in the treatment of such gastrointestinal disorders and diseases as duodenal ulcer and peptic ulcer. The compounds of this invention are also useful as antidiarheal agents.

The instant compounds may be used alone or in combination with other known antacids such as aluminum hydroxide, magnesium hydroxide, magnesium trisilicate, aluminum glycinate, calcium carbonate and the like.

The compounds of this invention possess blood-pressure-lowering activities and are also useful as antihypertensive agents.

The compounds described herein also possess useful anti-arrhythmic properties as well as useful local anesthetic properties.

For all these purposes, the heterocyclic alklene amidinoureas of this invention can be normally administered orally, parenterally or rectally. they may be administered as tables, aqueous or oily suspension, dispersible powders or granules, emulsions, hard or soft capsules, or syrups or elixirs. Parenterally, they may be administered as a salt in solution which pH is adjusted to physiologically accepted values. Aqueous solutions are preferred.

Compositions intended for oral use may be prepared according to any method known to the art for the manufacture of pharmaceutical compositions, and such compositions may contain one or more agents selected from the group consisting of sweetening agents, flavoring agents, coloring agents, preserving agents and the like, in order to provide a pharmaceutically elegant and palatable preparation.

The dosage regimen in carrying out the methods of this invention is that which ensures maximum therapeutic response until improvement is obtained, and thereafter the minimum effective level which gives relief. Thus, in general, the dosages are those that are therapeutically effective in the treatment of gastrointestinal disease conditions or symptoms, such as duodenal ulcer, peptic ulcer or diarrhea, and in the alleviation of hypertensive and arrhythmic disorders. The therapeutically effective doses correspond to those dosage amounts found effective in tests using animal models which are known to correlate to human activity for each particular disorder. In general, it is expected that daily doses between about 0.25 mg/kg and about 50 mg/kg (preferably in the range of about 0.5 –about 10 mg/kg/day) will be sufficient to produce the desired therapeutic effect, bearing in mind, of course, that in selecting the appropriate dosage in any specific case, consideration must be given to the patient's weight, general health, age, the severity of the disorder, and other factors which may influence response to the drug.

Various tests in animals have been carried out to show the ability of the compounds of this invention to exhibit reactions that can be correlated with activity in humans. These tests involve such factors as the effect of the heterocyclic alkylene amidinorureas on gastric secretion, their spasmolytic effect, their blood-pressure-lowering effect, and determination of their toxicity. It has been found that the compounds of this invention, when tested in the above variety of situations, show a marked activity.

One such test is the gastric secretion test. This test is carried out as follows: Shay rats are fasted for 4–8 hours and water is given ad lib. The rats are selected at random and separated into groups of ten. The animals are treated intraduodenally (I.D.) with the test compound or the vehicle immediately subsequent to the ligation of the stomach at the pyloric sphincter. The animals are sacrificed with chloroform at four hours post-drug-administration, the stomach removed and its contents assayed for volume, pH and total acids.

A second gastric secretion test is carried out on the dog. This is outlined in the *Handbook of Physiology*, Section 6: Alimentary Canal, Volume II: Secretion; American Physiology Society, Washington, D.C., 1967.

It has been found that the compounds of this invention, when subjected to the above gastric secretion tests, display marked ability to decrease gastric volume and gastric acidity. These tests are known to correlate well with gastric activity in humans and are standard tests used to determine antisecretory properties.

Determination of antispasmolytic properties can be carried out by the procedure outlined by D. A. Brodie and S. K. Kundrats in their article entitled "Effect of Drugs on Gastric Emptying in Rats," *Fed. Proc.* 24:714 (1965). Acute toxicity is calculated according to the standard Litchfield-Wilcoxon procedure.

Various tests can be carried out in animal models to show the ability of the amidinoureas of this invention to exhibit reactions that can be correlated with antidiarrheal activity in humans. The following tests show the ability of the compounds of this invention to inhibit diarrhea in animals and are known to correlate well with antidiarrheal activity in humans. These are considered to be standard tests used to determine antidiarrheal properties. This correlation can be shown by the activities of compounds known to be clinically active.

1. Fecal output in rat: The oral $ED_{50}$ (that dose which would be expected to reduce output by 50%) is determined by a method described by Bass et al., 1972. Briefly, the method involves dosing the rats and collecting the fecal output over an 8-hour period (4 P.M. –midnight) with the room darkened starting at 4:30 P.M.

Ref: Bass, P., Kennedy, J. A. and Willy, J. N.: Measurement of fecal output in rats. *Am. J. Dig. Dis.* 10:925–928, 1972.

2. Castor oil test in mice: Groups of mice are orally dosed with test compound and a half hour later all mice are given 0.3 ml of castor oil. Three hours after castor oil adminsistration, all mice are checked for diarrhea and the dose of testing compound which protected 50% of the mice from diarrhea is the $ED_{50}$ dose, p 3. Castor oil test in rats: The test is conducted according to Niermegeers et al., 1972. The rat is orally dosed with graded doses of test compound. One hour after dosing, each animal is challenged with 1 ml of castor oil orally. Fecal output is examined 1, 2, 3, 4, 6 and 8 hours after castor oil. Absence of diarrhea is the criterion of drug effectiveness.

Ref: Neimegeers, C. J. E., Lenaerts, F. M. and Janssen, P. A. J. Difenoxine, a potent, orally active and safe antidiarrheal agent in rats. *Arzneim-Forschung* (Drug. Res.) 22, 516–518, 1972.

Tests in animals have also been carried out to show the ability of compounds of this invention to inhibit reactions that can be correlated with antihypertensive effects in humans. One such test is outlined by Jacques de Champlain, Lawernce R. Krahoff and Julius Axelrod in *Circulation Research* XXIII:479 (1968). This testing method is known to correlate well with antihypertensive activity in humans and is a standard test used to determine antihypertensive properties. In view of the results of this test, the heterocyclic alkylene amidinoureas of this invention can be considered to be active antihypertensive agents.

The novel heterocyclic alkylene amidinoureas of this invention are useful in the treatment of parasitic infestations of a human host, particularly parasitic protozoal infestations in the genus Plasmodium.

Novel heterocyclic alkylene amidinoureas are also useful in the veterinary treatment of blood-residing diseases afflicting cattle, horses, sheep and dogs.

These compounds are useful in the treatment of veterinary diseases caused by parasitic helminths, particularly Filaria, and by parasitic protozoa, particularly Plasmodium and Babesia.

Microbiological tests can be carried out in model systems to show the ability of the heterocyclic alkylene amidinoureas of this invention to exhibit activity that can be correlated with anitprotozoal activity in humans and animals. The following microbiological test can show the ability of the compounds of this invention to inhibit parasitci protozoal growth and reproduction.

Antimalarial Blood Smear Test

Mice are injected intraperitoneally with 5,000,000 parasitized blood cells from a donor. Groups of ten mice receive inoculations administered subcutaneoulsly in doses ranging from 0.15 to 100 mg/kg, suspended in 0.5% methecel solution (doses expressed as base). The compound of interest is repeatedly injected on the day of inoculation (Day 1), Day 2 and Day 3. Blood smears are performed on Days 4, 5, 6 and 10 and the number of parasitic protozoa noted.

The compounds of this invention are also useful chelating agents for treating patients suffering from metal poisoning, for example, poisoning by magnesium, arsenic, chromium, manganese, cobalt, nickel, copper, zinc, cadmium silver, lead, antimony and mercury, by administering to a patient suffering from metal poisoning a therapeutically effective amount between 0.5 mg and 500 mg per dosage unit of at least one of said compounds.

We claim:

1. A compound of the formula $$R_1-(CH_2)_n-N(R_2)-\underset{\underset{}{\overset{X}{\|}}}{C}-NH-\underset{\underset{}{\overset{NH}{\|}}}{C}-N(R_5)(R_6)$$

wherein:
  n is 1 or 2;
  x is O or S;
  $R_1$ is one of the following heterocyclic groups:

$$(R)_m\text{-pyridine-N-oxide}, \quad (R)_m\text{-pyridine-N-oxide}, \quad (R)_m\text{-pyridine-N-oxide};$$

and the n-oxides thereof;
  $R_2$ is hydrogen or lower alkyl;
  $R_5$ and $R_6$ are hydrogen, lower alkyl, cycloalkyl of 3 to 6 carbon atoms, phenyl, lower alkenyl, lower alkoxy, benzyl or phenethyl;
and wherein:
  m is zero to four;
  R is a ring substituent selected from the group consisting of halogen, lower alkyl, lower alkenyl, phenyl, lower alkynyl, benzyl, phenethyl, nitro, cyano, sulfonyl, hydroxyl, carboxyl, lower alkanoyl, lower alkoxy, phenyl lower alkoxy, halo lower alkoxy, amido, amino, lower alkanoyloxy, lower alkylamino, lower alkoxyamino, and phenyl lower alkoxy amino;
  or a pharmaceutically acceptable salt thereof.

2. A compound of the formula $$R_1-(CH_2)_n-N(R_2)-\underset{\underset{}{\overset{X}{\|}}}{C}-NH-\underset{\underset{}{\overset{NH}{\|}}}{C}-N(R_5)(R_6)$$

wherein:
  n is 1 or 2;
  X is O or S;
  $R_1$ is one of the following heterocyclic groups:

$$(R)_m\text{-pyridine-N-oxide}, \quad (R)_m\text{-pyridine-N-oxide}, \quad (R)_m\text{-pyridine-N-oxide};$$

$R_2$ is hydrogen or lower alkyl;
  $R_5$ and $R_6$ are hydrogen, lower alkyl, cycloalkyl of 3 to 6 carbon atoms, phenyl, lower alkenyl, lower alkoxy, benzyl or phenethyl;
and wherein:
  m is zero to four;
  R is a ring substituent selected from the group consisting of halogen, lower alkyl, lower alkenyl, phenyl, lower alkynyl, benzyl, phenethyl, nitro, cyano, sulfonyl, hydroxyl, carboxyl, lower alkanoyl, lower alkoxy, phenyl lower alkoxy, halo lower alkoxy, amido, amino, lower alkanoyloxy, lower alkylamino, lower alkoxyamino, and phenyl lower alkoxy amino;
  or a pharmaceutically acceptable salt thereof.

3. A compound of the formula $$R_1-(CH_2)_n-N(H)-\underset{\underset{}{\overset{X}{\|}}}{C}-NH-\underset{\underset{}{\overset{NR_5}{\|}}}{C}-NHR_6$$

wherein:
  X may be oxygen or sulfur;
  n is 1 or 2;
  $R_1$ is selected from the group consisting of 2-pyridyl, 3-pyridyl and 4-pyridyl;
  $R_5$ and $R_6$ are hydrogen, lower alkyl; or a pharmaceutically acceptable or lower alkoxy salt thereof.

4. A compound of the formula

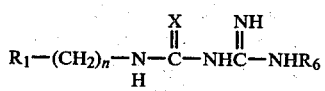

wherein: 'X may be oxygen or sulfur;
n is 1 or 2;
$R_1$ is selected from the group consisting of 2-pyridyl, 3-pyridyl and 4-pyridyl;
$R_6$ is hydrogen, lower alkyl, and; a pharmacuetically acceptable lower alkoxy; or salt thereof.

5. 1-propylamidino-3-(2-pyridyl-methyl)urea; or a pharmaceutically acceptable salt thereof.

6. 1-methylamidino-3-[2-(2'-pyridyl)-ethyl)]thiourea; or a pharmaceutically acceptable salt thereof.

7. A method for the treatment of gastrointestinal hyperacidity and ulcerogenic symptoms or disorders in mammals comprising administering thereto an effective amount of a compound according to claim 1.

8. A method for treating gastrointestinal spasms comprising administering to a patient suffering from said gastrointestinal spasms a thereapeutically effective amount of a compound according to claim 1.

9. A method for the treatment of diarrhea in humans and mammals which comprises the administering thereto of an effective amount of a compound according to claim 1.

10. A method for the treatment of arrhythmia in a patient suffering from arrhythmia which comprises administering to said patient an effective amount of a compound according to claim 1.

11. A method for the treatment of humans and mammals afflicted with parasitic infections of the blood and bloodforming organs, comprising administering to the afflicted host a composition containing an effective amount of a compound according to claim 1.

12. A method for lowering blood pressure in humans and other mammals which comprises administering an effective blood pressure-lowering amount of a compound according to the formula

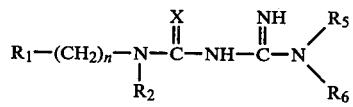

wherein:

n is 1 or 2;
X is O or S;
$R_1$ is one of the following heterocylic group:

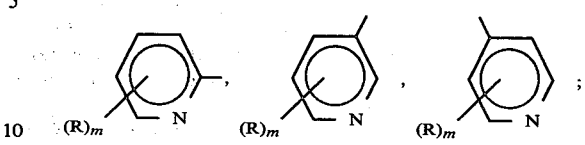

and the N-oxides thereof;
$R_2$ is hydrogen or lower alkyl;
$R_5$ and $R_6$ are hydrogen, lower alkyl, cycloalkyl of 3 to 6 carbon atoms, phenyl, lower alkenyl, lower alkoxy, benzyl or phenethyl;
and wherein:
m is 0 to 4;
R is a ring substitutent selected from the group consisting of halogen, lower alkyl, lower alkenyl, phenyl, lower alkynyl, benzyl, phenethyl, nitro, cyano, sulfonyl, hydroxyl, carboxyl, lower alkanoyl, lower alkoxy, phenyl lower alkoxy, halo lower alkoxy, amido, amino, lower alkanoyloxy, lower alkyl amino, lower alkoxy amino, and phenyl lower alkoxy amino;
or a pharmaceutically acceptable salt thereof.

13. A method for lowering blood pressure in humans and other mammals which comprises administering an effective blood pressure-lowering amount of a compound according to the formula

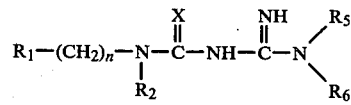

wherein:
n is 1 or 2;
X is O or S;
$R_1$ is selected from the group consisting of 2-pyridyl, 3-pyridyl and 4-pyridyl;
$R_2$ is hydrogen or lower alkyl;
$R_5$ and $R_6$ are hydrogen, lower alkyl or lower alkoxy;
or a pharmaceutically acceptable salt thereof.

14. A pharmaceutical composition comprising a blood pressure-lowering effective amount of a compound defined in claim 12 and a pharmaceutical carrier.

* * * * *

UNITED STATES PATENT AND TRADEMARK OFFICE
CERTIFICATE OF CORRECTION

PATENT NO. : 4,443,456
DATED : April 17, 1984
INVENTOR(S) : George H. Douglas et al It is certified that error appears in the above-identified patent and that said Letters Patent is hereby corrected as shown below:

| | |
|---|---|
| Col. 4, line 46 | "oxtyl" should read --octyl--. |
| Col. 4, line 53 | "to 6" should read --1 to 6--. |
| Col. 5, lines 21-22 | "hydroxyl" should read --hydroxy--. |
| Col. 5, line 33 | "sulphur" should read --sulfur--. |
| Col. 18, lines 15-20 | Between the formula at line 15 and the formula at line 20, insert: |

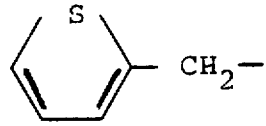        H        —CH$_3$

| | |
|---|---|
| Col. 18, line 45 | " -CH$_2$H$_5$ " should read -- -C$_2$H$_5$ --. |
| Col. 23, line 55 | " -CH$_2$ " should read -- -CH$_2$CH$_2$ --. |
| Col. 24, lines 15-20 | Between the formula at line 15 and the formula at line 20, insert: |

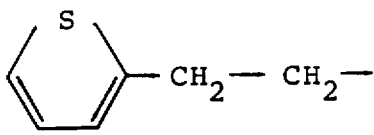        H        —CH$_3$

UNITED STATES PATENT AND TRADEMARK OFFICE
CERTIFICATE OF CORRECTION

PATENT NO. : 4,443,456
DATED : April 17, 1984
INVENTOR(S) : George H. Douglas et al It is certified that error appears in the above-identified patent and that said Letters Patent is hereby corrected as shown below:

| | |
|---|---|
| Col. 24, line 45 | " $-CH_2H5$ " should read -- $-C_2H_5$ --. |
| Col. 27, line 8 | "alklene" should read --alkylene--. |
| Col. 27, line 24 | "alklene" should read -alkylene--. |
| Col. 27, line 26 | Line 26 should read: --tered orally, parenterally or rectally. Orally, they may be ad- --. |
| Col. 27, line 27 | "tables" should read --tablets--. |

Signed and Sealed this

Twenty-seventh Day of October, 1987

Attest:

DONALD J. QUIGG

*Attesting Officer*  *Commissioner of Patents and Trademarks*